US010543185B2

(12) United States Patent
Noth et al.

(10) Patent No.: US 10,543,185 B2
(45) Date of Patent: Jan. 28, 2020

(54) METHOD FOR TREATING IDIOPATHIC PULMONARY FIBROSIS

(71) Applicants: The University of Chicago, Chicago, IL (US); Cornell University, Ithaca, NY (US)

(72) Inventors: Imre Noth, Chicago, IL (US); Justin Oldham, Chicago, IL (US); Fernando Martinez, Ithaca, NY (US)

(73) Assignees: The University of Chicago, Chicago, IL (US); Cornell University, Ithaca, NY (US)

(*) Notice: Subject to any disclaimer, the term of this patent is extended or adjusted under 35 U.S.C. 154(b) by 26 days.

(21) Appl. No.: 15/567,988

(22) PCT Filed: Apr. 20, 2016

(86) PCT No.: PCT/US2016/028361
§ 371 (c)(1),
(2) Date: Oct. 20, 2017

(87) PCT Pub. No.: WO2016/172150
PCT Pub. Date: Oct. 27, 2016

(65) Prior Publication Data
US 2018/0133184 A1 May 17, 2018

Related U.S. Application Data

(60) Provisional application No. 62/150,926, filed on Apr. 22, 2015.

(51) Int. Cl.
*A61K 31/198* (2006.01)
*A61K 31/52* (2006.01)
*A61K 31/573* (2006.01)
*A61P 11/00* (2006.01)
*C12Q 1/6883* (2018.01)

(52) U.S. Cl.
CPC ............ *A61K 31/198* (2013.01); *A61K 31/52* (2013.01); *A61K 31/573* (2013.01); *A61P 11/00* (2018.01); *C12Q 1/6883* (2013.01); *C12Q 2600/106* (2013.01)

(58) Field of Classification Search
None
See application file for complete search history.

(56) References Cited

U.S. PATENT DOCUMENTS

2014/0023696 A1   1/2014   Guilford
2014/0220570 A1   8/2014   Schwartz et al.

FOREIGN PATENT DOCUMENTS

EP          2589381 A1    5/2013
WO    WO 2014/121180    8/2014

OTHER PUBLICATIONS

Saher et al European Respiratory Society. Annual Congress 2013. "High-dose N-acetylcysteine (NAC) in fibrotic interstitial lung diseases, a retrospective analysis" Abstract No. 5353, Publication No. P2359.*
NCBI dbSNP Reference SNP Report for rs3750920, available via URL: <ncbi.nlm.nih.gov/snp/rs3750920#aliases_tab>, printed on May 1, 2019.*
Abecasis et al., "An integrated map of genetic variation from 1,092 human genomes" *Nature*, 491(7422):56-65, (2012).
Asehnoune et al., "Involvement of Reactive Oxygen Species in Toll-Like Receptor 4-Dependent Activation of NF-$\kappa$B" *J Immunol*, 172(4):2522-2529, (2004).
De Flora et al., "Attenuation of influenza-like symptomatology and improvement of cell-mediated immunity with long-term N-acetylcysteine treatment" *The European Respiratory Journal*, 10(7):1535-1541, (1997).
Fingerlin et al., "Genome-wide association study identifies multiple susceptibility loci for pulmonary fibrosis" *Nat Genet*. 45(6):613-620, (2013).
Han et al., "Lung microbiome and disease progression in idiopathic pulmonary fibrosis: an analysis of the COMET study" *Respiratory Medicine*, 2(7):548-556, (2014).
Hubbard et al., "Occupational exposure to metal or wood dust and aetiology of cryptogenic fibrosing alveolitis" *Lancet*, 347(8997):284-289, (1996).
International Preliminary Report on Patentability issued in International Application No. PCT/US2016/028361, dated Oct. 24, 2017.
International Search Report and Written Opinion issued in International Application No. PCT/US2016/028361, dated Jul. 29, 2016.
Janardhan et al., "Toll like receptor-4 expression in lipopolysaccharide induced lung inflammation" *Histology and Histopathology*, 21(7):687-696, (2006).
Johnson et al., "SNAP: a web-based tool for identification and annotation of proxy SNPs using HapMap" *Bioinformatics*, 24(24):2938-2939, (2008).
King et al., "Effect of interferon gamma-1b on survival in patients with idiopathic pulmonary fibrosis (INSPIRE): a multicenter, randomized, placebo-controlled trial" *Lancet* 374(9685):222-228, (2009).
Martinez et al., "Randomized Trial of acetylcysteine in Idiopathic Pulmonary Fibrosis" *N Engl J Med*. 370(22):2093-2101, (2014).
Molyneaux et al., "The Role of Bacteria in the Pathogenesis and progression of Idiopathic Pulmonary Fibrosis" *American Journal of Respiratory and Critical Care Medicine*, 190(8):906-913, (2014).

(Continued)

*Primary Examiner* — Carla J Myers
(74) *Attorney, Agent, or Firm* — Norton Rose Fulbright US LLP

(57) ABSTRACT

Aspects of the disclosure relate to a method for treating idiopathic pulmonary fibrosis (IPF) in a patient with N-acetylcysteine (NAC) comprising administering NAC to a patient after a sample from the patient has been genotyped and determined to be any one of: a) homozygous or heterozygous for a thymine at the single nucleotide polymorphism rs3750920; b) homozygous or heterozygous for guanine at the single nucleotide polymorphism rs5743894; or c) homozygous or heterozygous for thymine at the single nucleotide polymorphism rs35705950.

14 Claims, 3 Drawing Sheets

Specification includes a Sequence Listing.

(56) References Cited

OTHER PUBLICATIONS

Noth et al., "Genetic variants associated with idiopathic pulmonary fibrosis susceptibility and mortality: a genome-wide association study" *Lancet Respir Med*, 1(4):309-317, (2013).
Oddera et al., "N-Acetylcysteine enhances in vitro the intracellular killing of *Staphylococcus aureus* by human alveolar macrophages and blood polymorphonuclear leukocytes and partially protects phagocytes from self-killing" *The Journal of Laboratory and Clinical Medicine*, 124(2):293-301, (1994).
Oldham et al., "TOLLIP, MUC5B, and the Response to N-acetylcysteine Among Individuals with Idiopathic Pulmonary Fibrosis," *American Journal of Respiratory and Critical Care Medicine*, 192:1475-82, (2015).
Peljto et al., "Association Between the MUC5B Promoter Polymorphism and Survival in Patients With Idiopathic Pulmonary Fibrosis" *JAMA: The Journal of the American Medical Association*, 309(21):2232-2239, (2013).
Perez-Giraldo et al., "Influence of N-acetylcysteine on the formation of biofilm by *Staphylococcus epidermidis*" *The Journal of Antimicrobial Chemotherapy*, 39(5):643-646, (1997).
Pruitt et al., "RefSeq: an update on mammalian reference sequences" *Nucleic Acids Research*, 42:D756-763, (2014).
Raghu et al., "An Official ATS/ERS/JRS/ALAT Statement: Idiopathic Pulmonary Fibrosis: Evidence-based Guidelines for Diagnosis and Management" *American Journal of Respiratory and Critical Care Medicine*, 183(6):788-824, (2011).
Raghu et al., "Idiopathic Pulmonary Fibrosis: Clinical Meaningful Primary Endpoints in Phase 2 Clinical Trials" *American Journal of Respiratory and Critical Care Medicine*, 185(10):1044-1048, (2012).
Raghu et al., "Prednisone, Azathioprine, and N-Acetylcysteine for Pulmonary Fibrosis" *N Engl J Med*, 366(21):1968-1977, (2012).
Roy et al., "Muc5b is required for airway defense" *Nature*, 505(7483):412-416, (2014).
Saito et al., "Expression of toll-like receptor 2 and 4 in lipopolysaccharide-inducing lung injury in mouse" *Cell and Tissue Research*, 321(1):75-88, (2005).
Seibold et al., "A Common MUC5B Promoter Polymorphism and Pulmonary Fibrosis" *N Engl J Med*, 364(16):1503-1512, (2011).
Shah et al., "Human TOLLIP Regulates TLR2 and TLR4 Signaling and Its Polymorphisms Are Associated with Susceptibility to Tuberculosis" *J Immunol*, 189(4):1737-1746, (2012).
Tang et al., "Herpesvirus DNA Is Consistently Detected in Lungs of Patients with Idiopathic Pulmonary Fibrosis" *Journal of Clinical Microbiology*, 41(6):2633-2640, (2003).
Zhang et al., "A Variant in the Promoter of MUC5B and Idiopathic Pulmonary Fibrosis" *The New England Journal of Medicine*, 364(16):1576-1577, (2011).
Zhang et al., "Negative Regulation of Toll-like Receptor-mediated Signaling by Tollip" *The Journal of Biological Chemistry*, 277(9):7059-7065, (2002).
Extended European Search Report and Opinion for EP16783721.0, dated Dec. 7, 2018.

\* cited by examiner

METHOD FOR TREATING IDIOPATHIC PULMONARY FIBROSIS

CROSS-REFERENCE TO RELATED APPLICATIONS

This application is a national phase application under 35 U.S.C. § 371 of International Application No. PCT/US2016/028361 filed Apr. 20, 2016, which claims the benefit of priority of U.S. Provisional Patent Application No. 62/150,926, filed Apr. 22, 2015. The entire contents of each of the above-referenced disclosures are specifically incorporated herein by reference without disclaimer.

STATEMENT OF GOVERNMENT SUPPORT

This invention was made with government support under grant Nos: U10 HL080513 and T32 HL007605 awarded by the National Institutes of Health. The government has certain rights in the invention.

BACKGROUND

1. Field of the Invention

Embodiments of this disclosure are directed generally to biology and medicine. In certain aspects methods involve treating idiopathic pulmonary fibrosis.

2. Description of Related Art

Idiopathic pulmonary fibrosis (IPF) is a deadly fibrosing interstitial lung disease of unknown cause. Recent genome-wide association studies (GWAS) have shown single nucleotide polymorphisms (SNPs) within two protein-encoding genes, toll interacting protein (TOLLIP) and mucin 5B (MUC5B), to be associated with IPF among individuals of European ancestry (Noth I, et al., *The Lancet*. 2013; 1(4): 309-317 and Fingerlin T E, et al., *Nat Genet*. 2013; 45(6): 613-620). Single nucleotide polymorphisms (SNPs) within TOLLIP and MUC5B are associated with idiopathic pulmonary fibrosis (IPF) susceptibility and survival. Both genes play critical roles in lung host defense, a process that can be influenced by oxidative stress and modulated by N-acetyl-cysteine (NAC). However, previous reports have shown that NAC therapy was ineffective. A better understanding of the underlying molecular mechanisms of the disease as well as how different patient populations respond to therapeutic regimens will lead to more efficacious treatments for IPF.

SUMMARY

The current disclosure fulfills the aforementioned need in the art by providing novel therapeutic methods for treating IPF. Previous reports have shown that N-acetylcysteine (NAC) therapy provided no benefit in patients with IPF. However, it was found that NAC and PAN (another therapy for IPF comprising the combination of prednisone, azathioprine, and N-acetylcysteine) therapy provided a benefit to patients harboring certain single nucleotide polymorphisms (SNPs) within the TOLLIP or MUC5B genes. Furthermore, it was also found that, for patients harboring certain SNPs, NAC therapy is contraindicated, and could actually increase the risk of death in these patients, compared to not treating the patients. Therefore, the current methods not only provide for more effective therapeutic regimens, but may also prevent serious harmful side effects and even death by identifying individuals in which the therapy would increase the risk of such negative outcomes.

Aspects of the disclosure relate to a method for treating idiopathic pulmonary fibrosis (IPF) in a patient with N-acetylcysteine (NAC) comprising administering NAC to a patient after a sample from the patient has been genotyped and determined to be any one of: a) homozygous or heterozygous for a thymine at the single nucleotide polymorphism rs3750920; b) homozygous or heterozygous for guanine at the single nucleotide polymorphism rs5743894; or c) homozygous or heterozygous for thymine at the single nucleotide polymorphism rs35705950.

The term "genotype," as used herein refers to a chemical transformation of the patient's DNA to determine the sequence at the indicated location.

Methods of the disclosure provide for therapeutic regimens based on the determination of a patient's genotype with respect to certain polymorphisms. It was found that a patient may benefit or at least not be adversely affected from NAC or PAN therapy when the patient's genotype is CT or TT at the rs3750920 SNP. Further, it was found that a patient may have adverse effects to NAC or PAN therapy when the patient's genotype is CC at the rs3750920 SNP. A patient may benefit or at least not be adversely affected from NAC therapy with the patient's genotype is AG or GG at the rs5743894 SNP or GT or TT at the rs35705950 SNP. A patient may have adverse effects to NAC when the patient's genotype is AA at the rs5743894 SNP or GG at the rs35705950 SNP.

In some embodiments, the patient is determined to be homozygous for a thymine at the single nucleotide polymorphism rs3750920.

In some embodiments, the patient is administered NAC therapy. In some embodiments, the patient is administered a therapy comprising NAC and excluding prednisone and azathioprine.

A further aspect relates to a method for treating idiopathic pulmonary fibrosis (IPF) in a patient with a combination therapy comprising prednisone, azathioprine, and N-acetylcysteine (PAN) comprising administering PAN to a patient after a biological sample from the patient has been genotyped and determined to be homozygous or heterozygous for thymine at the single nucleotide polymorphism rs3750920.

A further aspect of the disclosure relates to a method for treating idiopathic pulmonary fibrosis in a patient in need thereof comprising: a) obtaining information indicating one or more of: i) the sequence of the rs3750920 SNP in the TOLLIP gene; ii) the sequence of the rs5743894 SNP in the non-coding region of the TOLLIP gene; or iii) the sequence of the rs35705950 SNP in the non-coding region of the MUC5B gene; b) treating the patient with NAC or PAN when the sequence of SNP rs3750920 is determined to be homozygous or heterozygous thymine; or treating the patient with NAC when the sequence of SNP rs5743894 or SNP rs35705950 is determined to be homozygous or heterozygous guanine or thymine, respectively; or c) not treating the patient with NAC or PAN and/or determining that NAC and/or PAN is contraindicated when the sequence of SNP rs3750920 is determined to be homozygous cytosine; or not treating the patient with NAC and/or determining that NAC is contraindicated when the sequence of SNP rs5743894 or SNP rs35705950 is determined to be homozygous alanine or guanine, respectively.

In some embodiments, portions or all of the MUC5B or TOLLIP gene in the patient's genomic DNA have been sequenced. In some embodiments, position 3074 upstream of the MUC5B gene has been sequenced. In some embodiments, position 581 in the nucleotide coding sequence of TOLLIP has been sequenced. In some embodiments, position 6120 in genomic DNA of the TOLLIP gene has been sequenced. In some embodiments, the method comprises amplifying at least a portion of chromosome 11. In some embodiments, the portion of chromosome 11 amplified comprises one or more SNP described herein and/or a SNP known to be associated with IPF. In some embodiments, sequencing comprises amplifying a nucleic acid sequence complementary or identical to a region of the MUC5B genomic DNA 3074 nucleotides upstream of the MUC5B gene.

In some embodiments, the patient was receiving one or more of NAC or PAN therapy prior to genotyping. In some embodiments, sequencing comprises amplifying a nucleic acid sequence complementary or identical to a region of the TOLLIP coding sequence that comprises position 581 or a region of the genomic DNA of the TOLLIP gene that comprises position 6120. In some embodiments, amplifying comprises using polymerase chain reaction (PCR).

Also encompassed within the methods described herein are further steps, such as obtaining a biological sample from the patient, evaluating a biological sample from a patient, obtaining sequence information on a patient, preparing or obtaining a report on the sequence of the patient. In some embodiments, the sequence of the patient refers to the sequence at an SNP described herein. In some embodiments, the biological sample is a blood sample, a fecal sample, or a mouth swab. Alternatively, the biological sample may be one described herein. In some embodiments, the biological sample comprises genomic DNA.

Aspects of the disclosure also relate to nucleic acids that can be used as probes or primers to detect and/or amplify a genomic sequence. Examples include SEQ ID NO: 1-20. Also included are nucleic acids that are complementary to these sequences and fragments of these sequences. The sequences may be modified with a modification known in the art or with a modification such as a dectable label and/or modified base. Also included are nucleic acids that hybridize adjacent to regions corresponding to SEQ ID NO:1-20 in the genomic DNA of a mammal. The nucleic acids of the disclosure may have a certain degree of identity such as at least, at most, or exactly about 60, 65, 70, 75, 80, 85, 90, 95, 96, 97, 98, 99, or 100% identity, or any derivable range therein.

In some embodiments, the patient has symptoms of or has been diagnosed with idiopathic pulmonary fibrosis. In some embodiments, the patient is a human patient.

In some embodiments, the patient is treated with NAC when the patient is determined to be homozygous or heterozygous for thymine at the single nucleotide polymorphism rs3750920 or wherein NAC therapy is determined to be contraindicated when the patient is determined to be homozygous for cytosine at the single nucleotide polymorphism rs3750920.

In some embodiments, position 3074 upstream of genomic DNA of MUC5B gene has been sequenced, position 581 in the nucleotide coding sequence of TOLLIP has been sequenced, and/or position 6120 in genomic DNA of the TOLLIP gene has been sequenced. In some embodiments, sequencing comprises amplifying a nucleic acid sequence complementary or identical to a region of the MUC5B genomic DNA 3074 nucleotides upstream of the MUC5B gene, a region of the TOLLIP coding sequence that comprises position 581, and/or a region of the genomic DNA of the TOLLIP gene that comprises position 6120.

In some embodiments, the patient has IPF, has been diagnosed with IPF, or is exhibiting symptomos or signs of IPF.

It is also contemplated that the term "knowing" is used according to its ordinary and plain meaning to refer to having the specified information. It is contemplated that typically a medical practitioner will be evaluating whether to prescribe or administer a particular therapeutic and in making that evaluation the practitioner will order one or more tests regarding sequence information of one or both of the patient's alleles or their encoded proteins. In the context of the polymorphisms discussed herein, the terms "allele" and "gene" are used interchangeably.

To achieve these methods, a doctor, medical practitioner, or their staff may obtain a biological sample for evaluation. The sample may be analyzed by the practitioner or their staff, or it may be sent to an outside or independent laboratory. The medical practitioner may be cognizant of whether the test is providing information regarding the patient's genotype at the SNPs described herein, or the medical practitioner may be aware only that the test indicates directly or indirectly that the genotype of the patient indicates that the patient should be administered a certain therapeutic regimen.

In any instance, the medical practitioner "knows" the relevant information that will allow him or her to determine the appropriate (or contraindicated) therapeutic regimen. It is contemplated that, for example, a laboratory conducts the test to determine that patient's genotype such that its personnel also know the appropriate information. They may report back to the practitioner with the specific result of the test performed or the laboratory may simply report that NAC or PAN is appropriate drug based on the laboratory results.

It is contemplated that embodiments may involve obtaining a biological sample from a patient. A biological sample is a sample that contains biological material such as all or part of an organ, tissue, cells, nucleic acids, proteins, or other such macromolecules and substances. The sample may include sputum, serum, blood, plasma, spinal fluid, semen, lymphatic fluid, urine, stool, pleural effusion, ascites, a tissue sample, tissue biopsy, cell swab, or a combination thereof. In other embodiments of the invention, a sample may include cells that are from lung, skin, muscle, liver, renal, colon, prostate, breast, brain, bladder, small intestine, large intestine, cervix, stomach, pancreas, testes, ovaries, bone, marrow, or spine. In some embodiments, the sample is a whole blood, plasma or serum sample, while in other embodiments, the sample is obtained by lavage, smear, or swab of an area on or in the patient. In certain embodiments, the biological sample is a blood sample.

In some embodiments, a patient's genotype with respect to a SNP described herein may already have been evaluated. It is contemplated that this analysis may have been done prior to the patient being considered for treatment with NAC or PAN or as part of a general examination. For example, a patient's genotype at various SNPs may be determined and entered into a database or entered into the patient's medical history. In this case, a medical practitioner may come to know what the sequence is by obtaining a patient history regarding the sequence at a particular location on chromosome 11.

The present disclosure also involves reporting the results of a determination of the nucleic acid sequence at the relevant position corresponding to a SNP described herein. Such a report would identify the patient by name, social security number, and/or other identification number or qualifier. It may also contain the actual data as a result of the determination or a summary of that data.

In some embodiments, methods include identifying a patient possibly in need of treatment with NAC or PAN. A patient for which NAC or PAN therapy is being considered as a treatment option may have symptoms of or may have been diagnosed with a medical condition, such as IPF. In certain embodiments, the patient has symptoms of or has been diagnosed with IPF.

Further aspects relate to kits for the detection of the SNPs described herein. The kits may comprise one or more nucleic acid probes or primers for the detection of an SNP described herein. The nucleic acids may be labeled with a detectable label. The kits may include one or more reagents for performing an assay described in the disclosure.

Other information may also be considered in determining an appropriate therapeutic regimen for the patient. This may include race, gender, age, previous surgeries, heart failure stage, patient history regarding cardiovascular disease, diagnosis of other diseases or conditions, risks for other diseases or condition, drug allergies, drug toxicity, and/or other medications being taken.

Use of the one or more compositions may be employed based on methods described herein. Other embodiments are discussed throughout this application. Any embodiment discussed with respect to one aspect applies to other aspects as well and vice versa. The embodiments in the Example section are understood to be embodiments that are applicable to all aspects of the technology described herein.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: increasing the chance of a certain endpoint, such as hospitalization-free survival and/or progression-free survival, reduces the symptoms of the disease or inhibits or stops the progression of the disease.

The term "therapeutically effective amount" refers to an amount of the drug that achieves a therapeutically desirable endpoint, such as treatment of symptoms, reducing the risk of hospitalization or death, or inhibits the progression of the disease.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
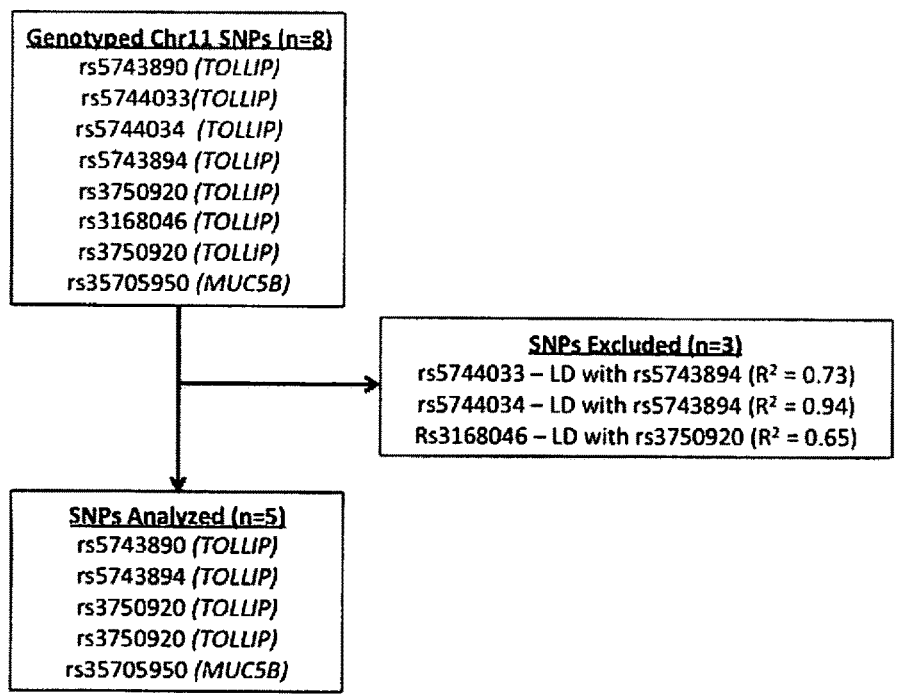
FIG. 1 shows the SNP selection. This figure is further described in Example 1.

The Applicants found that a patient's harboring certain SNPs in the TOLLIP and MUC5B genes exhibited a more favorable outcome after NAC or PAN therapy. Applicants also found that certain SNPs were associated with an increased risk of hospitalization or death after NAC or PAN therapy. This allows for the development of novel treatment methods that identify and treat patients based on their genetic makeup. These treatment methods not only identify patients that benefit from a certain treatment but also identify patients that may be harmed by a certain treatment.

I. IPF Therapy

A. N-acetylcysteine (NAC) Therapy

N-acetylcysteine is a pharmaceutical drug and nutritional supplement used primarily as a mucolytic agent and in the management of paracetamol (acetaminophen) overdose. NAC or (2R)-2-acetamido-3-sulfanylpropanoic acid, is a derivative of cysteine where an acetyl group is attached to the nitrogen atom. NAC serves as a prodrug to L-cysteine which is a precursor to the biologic antioxidant glutathione; hence administration of NAC replenishes glutathione stores. L-cysteine also serves as a precursor to cystine which in turn serves as a substrate for the cystine-glutamate antiporter on astrocytes hence increasing glutamate release into the extracellular space. This glutamate in turn acts on mGluR2/3 receptors, and at higher doses of acetylcysteine, mGluR5. Glutathione also modulates the NMDA receptor by acting at the redox site. NAC also possesses some anti-inflammatory effects possibly via inhibiting NF-κB and modulating cytokine synthesis.

Whereas other investigators previously reported that NAC therapy did not provide benefit for patients with IPF (N, Martinez et al., *N Engl J Med.* 2014; 370(22):2093-2101), the examples of the Application provide evidence that NAC therapy may reduce clinically meaningful end-point risk for genetically predisposed individuals, specifically those harboring certain SNPs in the TOLLIP and/or MUC5B genes. Without being limited to any scientific theory, it is contemplated that NAC therapy de-represses the innate immune response in the individuals that have SNPs associated with a favorable outcome with NAC therapy.

B. PAN Therapy

PAN therapy refers to a combination therapy of prednisone, azathioprine, and N-acetylcysteine. Prednisone (17, 21-dihydroxypregna-1,4-diene-3,11,20-trione) is a synthetic corticosteroid drug that is particularly effective as an immunosuppressant drug. It is used to treat certain inflammatory diseases (such as moderate allergic reactions) and (at higher doses) some types of cancer, but may have significant adverse effects.

Azathioprine is an immunosuppressive drug used in organ transplantation and autoimmune diseases and belongs to the chemical class of purine analogues. Synthesized originally as a cancer drug and a prodrug for mercaptopurine in 1957, it has been widely used as an immunosuppressant for more than 50 years. Azathioprine acts as a prodrug for mercaptopurine, inhibiting an enzyme required for the synthesis of DNA. Thus, it most strongly affects proliferating cells, such as the T cells and B cells of the immune system. One adverse effect of azathioprine may be bone marrow suppression, which can be life-threatening, especially in people with a genetic deficiency of the enzyme thiopurine S-methyltransferase. Azathioprine is produced by a number of manufacturers under different brand names (Azasan by Salix in the U.S., Imuran by GlaxoSmithKline in Canada, the U.S., Australia, Ireland and the United Kingdom, Azamun in Finland, and Imurel in Scandinavia and France, among others).

The enzyme thiopurine S-methyltransferase (TPMT) is responsible for various activation and deactivation steps in azathioprine's mechanism of action. The first metabolic step that azathioprine undergoes in the body is the conversion to 6-mercaptopurine (6-MP), which is itself an immunosuppressant prodrug. The TPMT enzyme is responsible, in part, for the methylation of 6-MP into the inactive metabolite 6-methylmercaptopurine—this methylation prevents 6-MP from further conversion into active, cytotoxic thioguanine nucleotide (TGN) metabolites.

II. Single Nucleotide Polymorphisms (SNPS)

A. TOLLIP

TOLLIP encodes toll-interacting protein (TOLLIP), an inhibitory adaptor protein, acting downstream from the toll-like receptors (TLRs), which are key mediators of the innate and adaptive immune response. The TOLLIP gene is located on human Chr 11 at position 1.3-1.33 MB, and the mRNA and protein sequence is represented in GenBank Accession Nos: NM_019009 and NP_061882, respectively. The sequences associated with these GenBank Accession Nos: are herein incorporated by reference.

1. rs3750920 SNP rs3750920 is a SNP known in the art and is further described in the NCBI SNP database that can be found on the world wide web at ncbi.nlm.nih.gov/projects/SNP. The SNP is located at position 1288726 on chromosome 11 and at position 581 of the TOLLIP mRNA and position 139 in the TOLLIP protein. As shown in table 2 of the examples, the CC genotype of this SNP (homozygous cysteine) results in a combined hazard ratio of 3.22 based on the endpoints of hospitalization-free survival and progression-free survival. Therefore, NAC would be contraindicated in people with the CC genotype, and those harboring the CC genotype have an increased risk of experiencing very harmful effects from NAC therapy. In contrast, individuals with a TT genotype had a hazard ratio of 0.14, which was statistically significant. Therefore, contrary to previous reports, NAC therapy does provide therapeutic benefits in individuals with IPF. Previous work with NAC failed to identify the population of individuals that would benefit from this therapy. The CT genotype also showed a reduced hazard ratio of 0.76, indicating that individuals with this genotype may have some benefits with NAC therapy.

2. rs5743894 SNP rs5743894 is a SNP known in the art and is further described in the NCBI SNP database that can be found on the world wide web at ncbi.nlm.nih.gov/projects/SNP. The SNP is located at position 1303542 on chromosome 11 and at position 6120 in a non-coding region in the genomic DNA of the TOLLIP gene. As shown in table 2 of the examples, the AA genotype of this SNP (homozygous alanine) results in a combined hazard ratio of 1.67, indicating that patient's harboring this genotype may have increased risks with NAC therapy. The hazard ration for patients with the AG or GG genotype is 0.33, indicating that these patients may benefit from NAC therapy.

B. MUC5B

MUC5B encodes a highly glycosylated mucin-5B precursor protein (Mucin-5B) involved in airway mucus production and maintaining immune homeostasis. The MUC5B gene is located on chromosome 11 at positions 1.24-1.28 Mb, and the mRNA and protein sequence is represented in GenBank Accession Nos: NM 002458 and NP_002449, respectively. The sequences associated with these GenBank Accession Nos: are herein incorporated by reference.

2. rs35705950 SNP rs35705950 is a SNP known in the art and is further described in the NCBI SNP database that can be found on the world wide web at ncbi.nlm.nih.gov/projects/SNP. The SNP is located at position 1219991 on chromosome 11 and at a position of 3074 upstream of the MUC5B gene. As shown in table 2 of the examples, the GG genotype of this SNP (homozygous guanine) results in a combined hazard ratio of 2.02, indicating that patient's harboring this genotype may have increased risks with NAC therapy. The hazard ration for patients with the GT or TT genotype is 0.60, indicating that these patients may benefit from NAC therapy.

III. Analysis of Polymorphism

A. Nucleic Acids

Certain embodiments concern various nucleic acids, including amplification primers, oligonucleotide probes, and other nucleic acid elements involved in the analysis of genomic DNA. In certain aspects, a nucleic acid comprises a wild-type, a mutant, or a polymorphic nucleic acid.

Embodiments of the disclosure also relate to kits comprising reagents necessary to perform the assays described throughout the disclosure.

The term "nucleic acid" is well known in the art. A "nucleic acid" as used herein will generally refer to a molecule (i.e., a strand) of DNA or RNA comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product.

In some embodiments, nucleic acids comprise or are complementary to all or 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1165, 1200, 1300, 1400, 1500 or more contiguous nucleotides, or any range derivable therein, of the human TOLLIP or MUC5B gene sequences or genomic sequences upstream or downstream of the gene.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

In particular aspects, a nucleic acid encodes a protein, polypeptide, or peptide. In certain embodiments, the present disclosure concerns novel compositions comprising at least one proteinaceous molecule. As used herein, a "proteinaceous molecule," "proteinaceous composition," "proteinaceous compound," "proteinaceous chain," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

1. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in European Patent 266,032, incorporated herein by reference, or via deoxynucleoside H-phosphonate intermediates as described by Froehler et al., 1986 and U.S. Pat. No. 5,705,629, each incorporated herein by reference. In the methods of the disclosure, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

2. Purification of Nucleic Acids

A nucleic acid may be purified on polyacrylamide gels, cesium chloride centrifugation gradients, chromatography columns or by any other means known to one of ordinary skill in the art (see for example, Sambrook et al., 2001, incorporated herein by reference). In some aspects, a nucleic acid is a pharmacologically acceptable nucleic acid. Pharmacologically acceptable compositions are known to those of skill in the art, and are described herein.

In certain aspects, the present disclosure concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

a. Nucleic Acid Segments

In certain embodiments, the nucleic acid is a nucleic acid segment. As used herein, the term "nucleic acid segment," are fragments of a nucleic acid. Thus, a "nucleic acid segment" may comprise any part of a gene sequence, including from about 2 nucleotides to the full length gene including promoter regions to the polyadenylation signal and any length that includes all the coding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

b. Nucleic Acid Complements

The present disclosure also encompasses a nucleic acid that is complementary to a nucleic acid. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule. In preferred embodiments, a complement is a hybridization probe or amplification primer for the detection of a nucleic acid polymorphism.

As used herein, the term "complementary" or "complement" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. However, in some diagnostic or detection embodiments, completely complementary nucleic acids are preferred.

3. Nucleic Acid Detection and Evaluation

Genotyping can be performed using methods known in the art. General methods of nucleic acid detection methods are provided below, followed by specific examples employed for the identification of polymorphisms, including single nucleotide polymorphisms (SNPs).

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense or coding) strand of a nucleic acid molecule is also intended to include the thymine (uridine), adenine, guanine, or cytosine (respectively) at the corresponding site on a minus (antisense or noncoding) strand of a complementary strand of a nucleic acid molecule. Thus, reference may be made to either strand and still comprise the same polymorphic site and an oligonucleotide may be designed to hybridize to either strand. Throughout the text, in identifying a polymorphic site, reference is made to the sense strand, only for the purpose of convenience.

Typically, the nucleic acid mixture is isolated from a biological sample taken from the individual, such as a blood sample or tissue sample using standard techniques. Suitable tissue samples include whole blood, semen saliva, tears, urine, fecal material, sweat, buccal, skin and hair. The nucleic acid mixture may be comprised of genomic DNA, mRNA, or cDNA and, in the latter two cases, the biological sample must be obtained from an organ in which the gene of interest (i.e. TOLLIP) is expressed. Furthermore it will be understood by the skilled artisan that mRNA or cDNA preparations would not be used to detect polymorphisms located in introns or in 5' and 3' nontranscribed regions. If a TOLLIP or MUC5B gene fragment is isolated, it must contain the polymorphic site(s) to be genotyped.

In the genotyping methods used, the identity of a nucleotide (or nucleotide pair) at a polymorphic site may be determined by amplifying a target region(s) containing the polymorphic site(s) directly from one or both copies of the gene in the individual and the sequence of the amplified region(s) determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

The target region(s) may be amplified using any oligonucleotide-directed amplification method, including but not limited to polymerase chain reaction (PCR) (U.S. Pat. No. 4,965,188), ligase chain reaction (LCR) (Barany et al., 1991; WO90/01069), and oligonucleotide ligation assay (OLA) (Landegren et al., 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, WO89/06700) and isothermal methods (Walker et al., 1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype for one or more polymorphic sites in a gene of an individual may also be determined by hybridization of one or both copies of the gene, or a fragment thereof, to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., 1985; Meyers et al., 1985) and proteins which recognize nucleotide mismatches, such as the E. coli mutS protein (Modrich, 1991). Alternatively, variant alleles can be identified by single strand conformation polymorphism (SSCP) analysis (Orita et al., 1989; Humphries, et al., 1996) or denaturing gradient gel electrophoresis (DGGE) (Wartell et al., 1990; Sheffield et al., 1989).

A polymerase-mediated primer extension method may also be used to identify the polymorphism(s). Several such methods have been described in the patent and scientific literature. Extended primers containing a polymorphism may be detected by mass spectrometry as described in U.S. Pat. No. 5,605,798. An other primer extension method is allele-specific PCR (Ruano et al., 1989); Ruano et al., 1991; WO 93/22456; Turki et al., 1995).

a. Hybridization

The use of a probe or primer of between 7, 8, 9, 10, 11, 12, 13, 14, 15, 16, 17, 18, 19, 20, 21, 22, 23, 24, 25, 50, 60, 70, 80, 90, or 100 nucleotides, preferably between 17 and 100 nucleotides in length, or in some aspects up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M NaHPO$_4$, 7% sodium dodecyl sulfate (SDS), 1 mM EDTA at 65° C., and washing in 0.1×SSC/ 0.1% SDS at 68° C. (Ausubel et al., 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/ 0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

In certain embodiments, it will be advantageous to employ nucleic acids of defined sequences in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used are disclosed in U.S. Pat. Nos. 5,849,481, 5,849,486 and 5,851,772. The relevant portions of these and other references identified in this section of the Specification are incorporated herein by reference.

b. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the TOLLIP or MUC5B gene locus or surrounding regions, or variants thereof, and fragments thereof are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCT/US89/01025, each of which is incorporated herein by reference in its entirety. Qbeta Replicase, described in PCT Application PCT/US87/00880, may also be used as an amplification method.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application 329 822 disclose a nucleic acid amplification process involving cyclically synthesizing single-stranded RNA ("ssRNA"), ssDNA, and double-stranded DNA (ds-DNA), which may be used in accordance with the methods described herein.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

c. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods of the disclosure.

Other methods of nucleic acid detection that may be used are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

d. Other Assays

Other methods for genetic screening may be used. For example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used are disclosed in U.S. Pat. Nos. 5,849,483, 5,851,770, 5,866,337, 5,925,525 and 5,928,870, each of which is incorporated herein by reference in its entirety.

e. DNA Sequencing

The most commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction may be utilized to facilitate the recovery of the desired genes (Mullis et al., 1986; European Patent Application 50,424; European Patent Application. 84,796, European Patent Application 258,017, European Patent Application. 237,362; European Patent Application. 201,184; U.S. Pat. Nos. 4,683,202; 4,582,788; and 4,683,194), all of the above incorporated herein by reference.

f. Exonuclease Resistance

Other methods that can be employed to determine the identity of a nucleotide present at a polymorphic site utilize a specialized exonuclease-resistant nucleotide derivative (U.S. Pat. No. 4,656,127). A primer complementary to an allelic sequence immediately 3'-to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

g. Microsequencing Methods

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

h. Extension in Solution

French Patent 2,650,840 and PCT Application WO91/02087 discuss a solution-based method for determining the identity of the nucleotide of a polymorphic site. According to these methods, a primer complementary to allelic sequences immediately 3'-to a polymorphic site is used. The identity of the nucleotide of that site is determined using labeled dideoxynucleotide derivatives which are incorporated at the end of the primer if complementary to the nucleotide of the polymorphic site.

i. Genetic Bit Analysis or Solid-Phase Extension

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

j. Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR have also been described (Nickerson et al., 1990). Here PCR is used to achieve the exponential amplification of target DNA, which is then detected using the OLA.

k. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

1. Invasive Cleavage Reactions

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the the target site ("target"). The upstream oligo and probe do not overlap but they contain contiguous sequences. The probe contains a donor fluorophore, such as fluoroscein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/quencher pair, which increases the amount of fluorescence that can be detected. See Lu et al., 2004.

In some cases, the assay is conducted on a solid-surface or in an array format.

m. Other Methods to Detect SNPs

Several other specific methods for polymorphism detection and identification are presented below and may be used as such or with suitable modifications in conjunction with identifying polymorphisms described herein. Several other methods are also described on the SNP web site of the NCBI on the World Wide Web at ncbi.nlm.nih.gov/SNP, incorporated herein by reference.

In a particular embodiment, extended haplotypes may be determined at any given locus in a population, which allows one to identify exactly which SNPs will be redundant and which will be essential in association studies. The latter is referred to as 'haplotype tag SNPs (htSNPs)', markers that capture the haplotypes of a gene or a region of linkage disequilibrium. See Johnson et al. (2001) and Ke and Cardon (2003), each of which is incorporated herein by reference, for exemplary methods.

The VDA-assay utilizes PCR amplification of genomic segments by long PCR methods using TaKaRa LA Taq reagents and other standard reaction conditions. The long amplification can amplify DNA sizes of about 2,000-12,000 bp. Hybridization of products to variant detector array (VDA) can be performed by a Affymetrix High Throughput Screening Center and analyzed with computerized software.

A method called Chip Assay uses PCR amplification of genomic segments by standard or long PCR protocols. Hybridization products are analyzed by VDA, Halushka et al. (1999), incorporated herein by reference. SNPs are generally classified as "Certain" or "Likely" based on computer analysis of hybridization patterns. By comparison to alternative detection methods such as nucleotide sequencing, "Certain" SNPs have been confirmed 100% of the time; and "Likely" SNPs have been confirmed 73% of the time by this method.

Other methods simply involve PCR amplification following digestion with the relevant restriction enzyme. Yet others involve sequencing of purified PCR products from known genomic regions.

In yet another method, individual exons or overlapping fragments of large exons are PCR-amplified. Primers are designed from published or database sequences and PCR-amplification of genomic DNA is performed using the following conditions: 200 ng DNA template, 0.5 µM each primer, 80 µM each of dCTP, dATP, dTTP and dGTP, 5% formamide, 1.5 mM $MgCl_2$, 0.5 U of Taq polymerase and 0.1 volume of the Taq buffer. Thermal cycling is performed and resulting PCR-products are analyzed by PCR-single strand conformation polymorphism (PCR-SSCP) analysis, under a variety of conditions, e.g, 5 or 10% polyacrylamide gel with 15% urea, with or without 5% glycerol. Electrophoresis is performed overnight. PCR-products that show mobility shifts are reamplified and sequenced to identify nucleotide variation.

In a method called CGAP-GAI (DEMIGLACE), sequence and alignment data (from a PHRAP.ace file), quality scores for the sequence base calls (from PHRED quality files), distance information (from PHYLIP dnadist and neighbour programs) and base-calling data (from PHRED '-d' switch) are loaded into memory. Sequences are aligned and examined for each vertical chunk ('slice') of the resulting assembly for disagreement. Any such slice is considered a candidate SNP (DEMIGLACE). A number of filters are used by DEMIGLACE to eliminate slices that are not likely to represent true polymorphisms. These include filters that: (i) exclude sequences in any given slice from SNP consideration where neighboring sequence quality scores drop 40% or more; (ii) exclude calls in which peak amplitude is below the fifteenth percentile of all base calls for that nucleotide type; (iii) disqualify regions of a sequence having a high number of disagreements with the consensus from participating in SNP calculations; (iv) removed from consideration any base call with an alternative call in which the peak takes up 25% or more of the area of the called peak; (v) exclude variations that occur in only one read direction. PHRED quality scores were converted into probability-of-error values for each nucleotide in the slice. Standard Baysian methods are used to calculate the posterior probability that there is evidence of nucleotide heterogeneity at a given location.

In a method called CU-RDF (RESEQ), PCR amplification is performed from DNA isolated from blood using specific primers for each SNP, and after typical cleanup protocols to remove unused primers and free nucleotides, direct sequencing using the same or nested primers.

In a method called DEBNICK (METHOD-B), a comparative analysis of clustered EST sequences is performed and confirmed by fluorescent-based DNA sequencing. In a related method, called DEBNICK (METHOD-C), comparative analysis of clustered EST sequences with phred quality >20 at the site of the mismatch, average phred quality >=20 over 5 bases 5'-FLANK and 3' to the SNP, no mismatches in 5 bases 5' and 3' to the SNP, at least two occurrences of each allele is performed and confirmed by examining traces.

In a method identified by ERO (RESEQ), new primers sets are designed for electronically published STSs and used to amplify DNA from 10 different mouse strains. The amplification product from each strain is then gel purified and sequenced using a standard dideoxy, cycle sequencing technique with $^{33}$P-labeled terminators. All the ddATP terminated reactions are then loaded in adjacent lanes of a sequencing gel followed by all of the ddGTP reactions and so on. SNPs are identified by visually scanning the radiographs.

In another method identified as ERO (RESEQ-HT), new primers sets are designed for electronically published murine DNA sequences and used to amplify DNA from 10 different mouse strains. The amplification product from each strain is prepared for sequencing by treating with Exonuclease I and Shrimp Alkaline Phosphatase. Sequencing is performed using ABI Prism Big Dye Terminator Ready Reaction Kit (Perkin-Elmer) and sequence samples are run on the 3700 DNA Analyzer (96 Capillary Sequencer).

FGU-CBT (SCA2-SNP) identifies a method where the region containing the SNP were PCR amplified using the primers SCA2-FP3 and SCA2-RP3. Approximately 100 ng of genomic DNA is amplified in a 50 ml reaction volume containing a final concentration of 5 mM Tris, 25 mM KCl, 0.75 mM $MgCl_2$, 0.05% gelatin, 20 pmol of each primer and 0.5 U of Taq DNA polymerase. Samples are denatured, annealed and extended and the PCR product is purified from a band cut out of the agarose gel using, for example, the QIAquick gel extraction kit (Qiagen) and is sequenced using dye terminator chemistry on an ABI Prism 377 automated DNA sequencer with the PCR primers.

In a method identified as JBLACK (SEQ/RESTRICT), two independent PCR reactions are performed with genomic DNA. Products from the first reaction are analyzed by sequencing, indicating a unique FspI restriction site. The mutation is confirmed in the product of the second PCR reaction by digesting with Fsp I.

In a method described as KWOK(1), SNPs are identified by comparing high quality genomic sequence data from four randomly chosen individuals by direct DNA sequencing of PCR products with dye-terminator chemistry (see Kwok et al., 1996). In a related method identified as KWOK(2) SNPs are identified by comparing high quality genomic sequence data from overlapping large-insert clones such as bacterial artificial chromosomes (BACs) or P1-based artificial chromosomes (PACs). An STS containing this SNP is then developed and the existence of the SNP in various populations is confirmed by pooled DNA sequencing (see Taillon-Miller et al., 1998). In another similar method called KWOK (3), SNPs are identified by comparing high quality genomic sequence data from overlapping large-insert clones BACs or PACs. The SNPs found by this approach represent DNA sequence variations between the two donor chromosomes but the allele frequencies in the general population have not yet been determined. In method KWOK(5), SNPs are identified by comparing high quality genomic sequence data from a homozygous DNA sample and one or more pooled DNA samples by direct DNA sequencing of PCR products with dye-terminator chemistry. The STSs used are developed from sequence data found in publicly available databases. Specifically, these STSs are amplified by PCR against a complete hydatidiform mole (CHM) that has been shown to be homozygous at all loci and a pool of DNA samples from 80 CEPH parents (see Kwok et al., 1994).

In another such method, KWOK (OverlapSnpDetectionWithPolyBayes), SNPs are discovered by automated computer analysis of overlapping regions of large-insert human genomic clone sequences. For data acquisition, clone sequences are obtained directly from large-scale sequencing centers. This is necessary because base quality sequences are not present/available through GenBank. Raw data processing involves analyzed of clone sequences and accompanying base quality information for consistency. Finished ('base perfect', error rate lower than 1 in 10,000 bp) sequences with no associated base quality sequences are assigned a uniform base quality value of 40 (1 in 10,000 bp error rate). Draft sequences without base quality values are rejected. Processed sequences are entered into a local database. A version of each sequence with known human repeats masked is also stored. Repeat masking is performed with the program "MASKERAID." Overlap detection: Putative overlaps are detected with the program "WUBLAST." Several filtering steps followed in order to eliminate false overlap detection results, i.e. similarities between a pair of clone sequences that arise due to sequence duplication as opposed to true overlap. Total length of overlap, overall percent similarity, number of sequence differences between nucleotides with high base quality value "high-quality mismatches." Results are also compared to results of restriction fragment mapping of genomic clones at Washington University Genome Sequencing Center, finisher's reports on overlaps, and results of the sequence contig building effort at the NCBI. SNP detection: Overlapping pairs of clone sequence are analyzed for candidate SNP sites with the 'POLYBAYES' SNP detection software. Sequence differences between the pair of sequences are scored for the probability of representing true sequence variation as opposed to sequencing error. This process requires the presence of base quality values for both sequences. High-scoring candidates are extracted. The search is restricted to substitution-type single base pair variations. Confidence score of candidate SNP is computed by the POLYBAYES software.

In method identified by KWOK (TaqMan assay), the TaqMan assay is used to determine genotypes for 90 random individuals. In method identified by KYUGEN(Q1), DNA samples of indicated populations are pooled and analyzed by PLACE-SSCP. Peak heights of each allele in the pooled analysis are corrected by those in a heterozygote, and are subsequently used for calculation of allele frequencies. Allele frequencies higher than 10% are reliably quantified by this method. Allele frequency=0 (zero) means that the allele was found among individuals, but the corresponding peak is not seen in the examination of pool. Allele frequency=0-0.1 indicates that minor alleles are detected in the pool but the peaks are too low to reliably quantify.

In yet another method identified as KYUGEN (Method1), PCR products are post-labeled with fluorescent dyes and analyzed by an automated capillary electrophoresis system under SSCP conditions (PLACE-SSCP). Four or more individual DNAs are analyzed with or without two pooled DNA (Japanese pool and CEPH parents pool) in a series of experiments. Alleles are identified by visual inspection. Individual DNAs with different genotypes are sequenced and SNPs identified. Allele frequencies are estimated from peak heights in the pooled samples after correction of signal bias using peak heights in heterozygotes. For the PCR primers are tagged to have 5'-ATT or 5'-GTT at their ends for post-labeling of both strands. Samples of DNA (10 ng/ul) are amplified in reaction mixtures containing the buffer (10 mM Tris-HCl, pH 8.3 or 9.3, 50 mM KCl, 2.0 mM $MgCl_2$), 0.25 µM of each primer, 200 µM of each dNTP, and 0.025 units/µl of Taq DNA polymerase premixed with anti-Taq antibody. The two strands of PCR products are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. For the SSCP: an aliquot of fluorescently labeled PCR products and TAMRA-labeled internal markers are added to deionized formamide, and denatured. Electrophoresis is performed in a capillary using an ABI Prism 310 Genetic Analyzer. Genescan softwares (P-E Biosystems) are used for data collection and data processing. DNA of individuals (two to eleven) including those who showed different genotypes on SSCP are subjected for direct sequencing using big-dye terminator chemistry, on ABI Prism 310 sequencers. Multiple sequence trace files obtained from ABI Prism 310 are processed and aligned by Phred/Phrap and viewed using Consed viewer. SNPs are identified by PolyPhred software and visual inspection.

In yet another method identified as KYUGEN (Method2), individuals with different genotypes are searched by denaturing HPLC (DHPLC) or PLACE-SSCP (Inazuka et al., 1997) and their sequences are determined to identify SNPs. PCR is performed with primers tagged with 5'-ATT or 5'-GTT at their ends for post-labeling of both strands. DHPLC analysis is carried out using the WAVE DNA fragment analysis system (Transgenomic). PCR products are injected into DNASep column, and separated under the conditions determined using WAVEMaker program (Transgenomic). The two strands of PCR products that are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. SSCP followed by electrophoresis is performed in a capillary using an ABI Prism 310 Genetic Analyzer. Genescan softwares (P-E Biosystems). DNA of individuals including those who showed different genotypes on DHPLC or SSCP are subjected for direct sequencing using big-dye terminator chemistry, on ABI Prism 310 sequencer. Multiple sequence trace files obtained from ABI Prism 310 are processed and aligned by Phred/Phrap and viewed using Consed viewer. SNPs are identified by PolyPhred software and visual inspection. Trace chromatogram data of EST sequences in Unigene are processed with PHRED. To identify likely SNPs, single base mismatches are reported from multiple sequence alignments produced by the programs PHRAP, BRO and POA for each Unigene cluster. BRO corrected possible misreported EST orientations, while POA identified and analyzed non-linear alignment structures indicative of gene mixing/chimeras that might produce spurious SNPs. Bayesian inference is used to weigh evidence for true polymorphism versus sequencing error, misalignment or ambiguity, misclustering or chimeric EST sequences, assessing data such as raw chromatogram height, sharpness, overlap and spacing; sequencing error rates; context-sensitivity; cDNA library origin, etc.

In method identified as MARSHFIELD (Method-B), overlapping human DNA sequences which contained putative insertion/deletion polymorphisms are identified through searches of public databases. PCR primers which flanked each polymorphic site are selected from the consensus sequences. Primers are used to amplify individual or pooled human genomic DNA. Resulting PCR products are resolved on a denaturing polyacrylamide gel and a PhosphorImager is used to estimate allele frequencies from DNA pools.

4. Linkage Disequilibrium

Polymorphisms in linkage disequilibrium with another polymorphism in which identification of one polymorphism is predictive of the identity of the linked polymorphism. "Linkage disequilibrium" ("LD" as used herein, though also referred to as "LED" in the art) refers to a situation where a particular combination of alleles (i.e., a variant form of a given gene) or polymorphisms at two loci appears more frequently than would be expected by chance. "Significant" as used in respect to linkage disequilibrium, as determined by one of skill in the art, is contemplated to be a statistical p or a value that may be 0.25 or 0.1 and may be 0.1, 0.05, 0.001, 0.00001 or less. A polymorphism described herein may be determined by evaluating the nucleic acid sequence of a polymorphism in linkage disequilibrium with the polymorphism described herein. The methods of the disclosure may be implemented in this manner with respect to one or more polymorphisms so as to allow haplotype analysis. "Haplotype" is used according to its plain and ordinary meaning to one skilled in the art. It refers to a collective genotype of two or more alleles or polymorphisms along one of the homologous chromosomes.

IV. Therapy

Once the genotype of the individual is determined with respect to a particular polymorphism or SNP, a therapeutic course of treatment may be individualized. In a preferred embodiment of the method, the trait of interest is a clinical response exhibited by a patient to some therapeutic treatment, for example, response to a therapeutic regimen such as NAC or PAN.

A. Routes of Administration

Administration of the therapeutic may be by any number of routes including, but not limited to oral, intravenous, intramuscular, intra-arterial, intramedullary, intrathecal, intraventricular, intradermal, intratracheal, intravesicle, intraocular, transdermal, subcutaneous, intraperitoneal, intranasal, enteral, topical, sublingual, or rectal. Further details on techniques for formulation and administration may be found in the latest edition of Remington's Pharmaceutical Sciences (Maack Publishing Co., Easton, Pa.). In certain embodiments the therapeutics are formulated for oral administration.

B. Formulations

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients, its use in therapeutic compositions is contemplated. Supplementary active ingredients also can be incorporated into the compositions, provided they do not inactivate the vectors or cells of the compositions.

The active compositions may include classic pharmaceutical preparations. Administration of these compositions may be via any common route so long as the target tissue is available via that route. This includes oral, nasal, or buccal.

Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For oral administration the therapeutics generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

C. Dosages

The amount of therapeutic that is administered or prescribed to the patient can be about, at least about, or at most about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg, or any range derivable therein. Alternatively, the amount administered or prescribed may be about, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 mg/kg, or any range derivable therein, with respect to the weight of the patient.

When provided in a discrete amount, each intake of a therapeutic can be considered a "dose." A medical practitioner may prescribe or administer multiple doses of a particular therapeutic over a particular time course (treatment regimen) or indefinitely.

The therapeutic may be administered 1, 2, 3, 4, 5, 6, 7, 8, 9, 10, 11, 12, 13, 14, 15, 16, 17, 18, 19, 20, 30, 40, 50, 60, 70, 80, or more times or any range derivable therein. It is further contemplated that the drug may be taken for an indefinite period of time or for as long as the patient exhibits symptoms of the medical condition for which the therapeutic was prescribed or administered. Also, the drug may be administered every 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more, or any range derivable therein. Alternatively, it may be administered systemically over any such period of time and be extended beyond more than a year.

D. Other Therapeutic Options

In certain embodiments, methods may involve administering a an additional therapeutic for treating IPF or for treating or alleviating the symptoms associated with IPF.

As a second therapeutic regimen, the agent may be administered or taken at the same time, or either before or after the NAC or PAN therapy. The treatment may improve one or more symptoms of IPF and/or decrease disease-related morbidity and mortality.

Combinations may be achieved by administering a single composition or pharmacological formulation that includes both agents, or by contacting the cell with two distinct compositions or formulations, at the same time. Alternatively, the NAC or PAN therapy may precede or follow administration of the other agent(s) by intervals ranging from minutes to weeks. In embodiments where the other agent are administered separately from one another, one would generally ensure that a significant period of time did not expire between the time of each delivery, such that the agent would still be able to exert an advantageously combined effect.

It also is conceivable that more than one administration of either NAC, PAN, or the other agent will be desired. In this regard, various combinations may be employed. By way of illustration, where NAC or PAN "A" and the other agent is "B", the following permutations based on 3 and 4 total administrations are exemplary:

A/B/A B/A/B B/B/A A/A/B B/A/A A/B/B B/B/B/A B/B/A/B
A/B

A/A/B/B A/B/A/B A/B/B/A B/B/A/A B/A/B/A B/A/A/B
B/B/B/A

A/A/A/B B/A/A/A A/B/A/A A/A/B/A A/A/A/B/B B/A/B/B
B/B/A/B

Other combinations are likewise contemplated.

V. Examples

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: TOLLIP and MUC5B Polymorphisms and the Response to N-Acetylcysteine in Patients with Idiopathic Pulmonary Fibrosis Single nucleotide polymorphisms (SNPs) within TOLLIP and MUC5B are associated with idiopathic pulmonary fibrosis (IPF) susceptibility and survival. Both genes play critical roles in lung host defense, a process that can be influenced by oxidative stress and modulated by N-acetylcysteine (NAC). Applicants set out to determine whether SNPs within TOLLIP and MUC5B modify the efficacy of NAC therapy in patients with IPF. To achieve this, secondary analysis was completed of the PANTHER-IPF clinical trial (n=154) and an independent replication cohort (n=405) composed of patients from the INSPIRE clinical trial and University of Chicago. SNPs within TOLLIP (rs5743890/rs5743894/rs5743854/rs3750920) and MUC5B (r535705950) were genotyped. Multivariable Cox regression with interaction analysis was performed followed by genotype-stratified models for significant interaction SNPs to determine genotype-specific survival associated with NAC therapy. A composite endpoint of death, FVC decline, hospitalization or transplantation was used.

As described in further detail below, significant interaction was observed between NAC therapy and rs3750920 (TOLLIP) ($p_{Interaction}$=0.002). Compared to placebo, NAC therapy was associated with a significant reduction in endpoint risk among those with an rs3750920 TT genotype (HR 0.14; 95% CI 0.02-0.83; p=0.03). A trend towards increased risk was observed among NAC recipients with an rs3750920 CC genotype (HR 3.23; 95% CI 0.79-13.16; p=0.10). Carrying one or more rs35705950 (MUC5B) T alleles was also associated with a significantly improved progression-free survival (HR 0.32; 95% CI 0.11-0.94; p=0.04) in those receiving NAC therapy. Similar interaction between NAC therapy and rs3750920 (TOLLIP) was observed in the replication cohort.

Whereas PANTHER investigators previously showed that NAC therapy provided no benefit in patients with IPF, here we demonstrate that NAC may reduce clinically meaningful endpoint risk in genetically susceptible individuals. This study highlights the importance of drug-gene interaction in IPF clinical trials, draws attention to the role of genes involved in airway host defense and reignites the question of whether NAC may be an effective therapy for some patients with IPF.

Idiopathic pulmonary fibrosis (IPF) is a deadly fibrosing interstitial lung disease of unknown cause. Recent genome-wide association studies (GWAS) have shown single nucleotide polymorphisms (SNPs) within two protein-encoding genes, toll interacting protein (TOLLIP) and mucin 5B (MUC5B), to be associated with IPF among individuals of European ancestry (Noth I, et al., *The Lancet.* 2013; 1(4): 309-317 and Fingerlin T E, et al., *Nat Genet.* 2013; 45(6): 613-620). SNPs within these genes have also been associated with survival in this population (Noth I, et al., *The Lancet.* 2013; 1(4):309-317 and Peljto A L, Zhang Y, et al., *JAMA: the journal of the American Medical Association.* 2013; 309(21):2232-2239). TOLLIP and MUC5B reside in close vicinity on chromosome 11p15.5 and have distinct biological functions that may be related to IPF pathogenesis. TOLLIP encodes toll-interacting protein (TOLLIP), an inhibitory adaptor protein, acting downstream from the toll-like receptors (TLRs), which are key mediators of the innate and adaptive immune response, (Zhang G, Ghosh S. *The Journal of biological chemistry.* 2002; 277(9):7059-7065 and Pruitt K D, et al., *Nucleic acids research.* 2014; 42 (Database issue):D756-763) whereas MUC5B encodes a highly glycosylated mucin-5B precursor protein (Mucin-5B) involved in airway mucus production and maintaining immune homeostasis (Pruitt K D, et al., *Nucleic acids research.* 2014; 42 (Database issue):D756-763 and Roy M G, et al., Nature. 2014; 505(7483):412-416).

Airway host defense, a process in which TOLLIP and MUC5B participate through immune signaling, Roy M G, et al., *Nature.* 2014; 505(7483):412-416; Shah J A, et al., *J Immunol.* 2012; 189(4):1737-1746; Saito T, et al., Cell and tissue research. 2005; 321(1):75-88; and Janardhan K S, et al., *Histology and histopathology.* 2006; 21(7):687-696) appears to play a critical role in IPF, as viral and bacterial colonization, along with particle inhalation, has been implicated in disease onset and progression (Tang Y W, et al., *Journal of clinical microbiology.* 2003; 41(6):2633-2640;

Han M K, et al., *The lancet. Respiratory medicine.* 2014; 2(7):548-556; Hubbard R, et al., *Lancet.* 1996; 347(8997): 284-289; and Molyneaux P L, et al., *American journal of respiratory and critical care medicine.* 2014; 190(8):906-913). Because the airway immune response can be influenced by presence of reactive oxygen species and other forms of oxidative stress (Asehnoune K, et al., *J Immunol.* 2004; 172(4):2522-2529 and De Flora S, et al., *The European respiratory journal.* 1997; 10(7):1535-1541), it was hypothesized that polymorphisms within TOLLIP and/or MUC5B modulate the efficacy of N-acetylcysteine (NAC), an antioxidant used to treat IPF. Using a candidate gene approach, Applicants tested this hypothesis in patients enrolled in the Idiopathic Pulmonary Fibrosis Clinical Research Network (IPFnet) clinical trial "Evaluating the Effectiveness of Prednisone, Azathioprine, and N-Acetylcysteine in Patients with Idiopathic Pulmonary Fibrosis" (PANTHER-IPF)(Martinez F J, et al., *N Engl J Med.* 2014; 370(22):2093-2101 and Raghu G, et al., *N Engl J Med.* 2012; 366(21):1968-1977). Applicants then analyzed an independent cohort of patients drawn from the University of Chicago and "The INSPIRE Trial: A Study of Interferon Gamma-1b for Idiopathic Pulmonary Fibrosis" (King T E, et al., *Lancet.* 2009; 374(9685):222-228) to determine whether the findings could be replicated.

Five SNPs were chosen to conduct this analysis. rs5743890 and rs5743894 reside within non-coding TOLLIP regulatory regions and are associated with IPF susceptibility and survival (r55743890 only). rs3750920 is a synonymous coding SNP residing within TOLLIP exon 3, was marginally associated with IPF in two GWAS discovery cohorts and has been shown to mediate the pulmonary immune response vis-à-vis TLR2 and TLR4 signaling. rs5743854 is located within the TOLLIP promoter and has potential function consequences. rs35705950 resides within the promoter of MUC5B and is associated with IPF susceptibility and improved survival.

Methods

Study Cohorts:

The PANTHER cohort consists of individuals enrolled in the IPFnet randomized clinical trial comparing three treatments: prednisone/azathioprine/N-acetylcysteine (PAN) combination therapy, N-acetylcysteine (NAC) monotherapy and placebo. Participants were enrolled from December 2009 to October 2011, at which time the PAN arm was stopped after interim analysis showed an increased risk of death and hospitalization in this group. Enrollment resumed for the NAC and placebo arms from January to July 2012, with study completion in 2013. Clinical and genetic data for patients providing informed consent to genetic testing were used to conduct the analysis. Patients were followed for up to 72 weeks after randomization.

The INSPIRE cohort consists of individuals enrolled in the industry-sponsored randomized clinical trial comparing interferon gamma-1b to placebo. Participants were enrolled from December 2003 to April 2006 at which time the trial was stopped early after interim analysis showed no benefit with interferon gamma-1b compared to placebo. Clinical and genetic data for patients providing informed consent to genetic testing were used to conduct the analysis. Patients were followed for up to 170 weeks after randomization.

The University of Chicago (UChicago) cohort consists of individuals followed in the UChicago ILD clinic from 2007-2013 who provided informed consent to undergo DNA testing. Patients were followed from time of initial evaluation until death, lung transplantation, loss-to-follow up or time of censoring (Sep. 9, 2013). Vital status was determined using telephone interviews with family members and the social security death index. Patients participating in PANTHER and INSPIRE were removed from the UC cohort. Patients were excluded if they did not have at least two sets of pulmonary function tests for analysis.

To minimize the effects of population stratification, only participants that self-declared a non-Hispanic white ethnicity were included in the analysis. Demographic and clinical information extracted from the datasets included age, gender, race/ethnicity, treatment arm, pulmonary function testing (PFT) including forced vital capacity (FVC) and diffusion capacity for carbon monoxide (DLCO) and outcomes, including death, >10% decline in FVC, hospitalization and lung transplantation.

SNP selection and Genotyping:

Eight SNPs at the chr11p15.5 locus were genotyped. Of those, three were excluded due to the presence of moderate-to-strong linkage disequilibrium (LD) with another SNP based on SNP annotation and proxy search program (SNAP) R-squared approximation using 1000 genomes project data (FIG. 1). Genotypes for the PANTHER cohort were determined with TaqMan allelic discrimination assays (Applied Biosystems, Foster City, Calif.). This was followed by Sanger sequencing to confirm TaqMan calls and account for missing data. Genotypes for those in the INSPIRE cohort were determined using the iPLEX Gold™ Platform (Sequenom, San Diego, Calif.), while UC cohort genotypes were determined by HiSeq2000 (Illumina, San Diego, Calif.) sequencing. DNA was extracted from peripheral blood using QIAamp® DNA Blood Maxi kit from Qiagen (Valencia, Calif.) following manufacturer's protocol. DNA concentration was quantified using Cytation™3 Cell Imaging Multi-Mode Reader (BioTek® Instruments, Inc., Winooski, Vt.). Genotypes for the PANTHER cohort were determined with TaqMan allelic discrimination assays (Applied Biosystems, Foster City, Calif.) on a 7900HT Fast Real-Time PCR System with automated calls generated by using the SDS software based on discriminating plots (95% confidence). Given the repetitive content of the DNA sequences surrounding these genes and missing information for some SNPs with the TaqMan assays, all samples were also sequenced by Sanger method.

Polymorphic DNA Technologies, Inc., (Alameda, Calif.) services were used for Sanger sequencing calls. A two-step "boost/nest" PCR strategy was applied, in which a boost reaction with a larger fragment was performed first, which then served as a template for the "nested" amplification and sequencing by using the nest primers below.

Primers used for Genotyping by Sanger

| Amplicon | Boost forward primer (5'→3') | SEQ ID NO: | Boost reverse primer (5'→3') | SEQ ID NO: | Size* | Nest forward primer (5'→3') | SEQ ID NO: | Nest reverse primer (5'→3') | SEQ ID NO: | Size* |
|---|---|---|---|---|---|---|---|---|---|---|
| rs5743890 | TTTCTCTCATTGCCTTTTGAAT | 1 | GAGACACCAGAAGGGA | 6 | 437 | GTTGTTTTATCTCAAGTACATACA | 11 | GAGAAACACAGAAGGAAATC | 16 | 323 |

-continued

| Primers used for Genotyping by Sanger | | | | | | | | | |
|---|---|---|---|---|---|---|---|---|---|
| Amplicon | Boost forward primer (5'→3') | SEQ ID NO: | Boost reverse primer (5'→3') | SEQ ID NO: | Size* | Nest forward primer (5'→3') | SEQ ID NO: | Nest reverse primer (5'→3') | SEQ ID NO: | Size* |
| rs5743894 | TCTAAC ACTGTC CCTTGA | 2 | CAAAAG CCAGTC AAGCAG | 7 | 458 | ACAGG CCCCT GGTTA | 12 | GAGATC CAGAGA GGGA | 17 | 376 |
| rs3750920 | ATATAC GATCGT GAAGCC | 3 | GTGAGC CCTGCT GTT | 8 | 502 | GTGTT GGTGC AGGTG | 13 | TATGGG CTCAGT GCC | 18 | 395 |
| rs5743854 | TTCAGC CTCAGT TTACC | 4 | ATGACG GTTGTC GGC | 9 | 469 | TGGAG TCGCT CTGGT | 14 | TCTGGG CAGTGG GTT | 19 | 428 |
| rs35705950 | TCCACC CTGGAA CAG | 5 | CCCCTT TGTCTC CACT | 10 | 478 | TGACA CCAAA CAAGT GG | 15 | TGGCCA GAATGA GGG | 20 | 402 |

*Amplicon products in base pairs.

A comparison of TaqMan and Sanger sequencing calls is shown below. Calls were highly correlated with regard to all SNPs with the exception of rs5743854, where a less strong correlation was observed.

| Taqman and Sanger genotype calls and correlation | | | |
|---|---|---|---|
| SNP | Taqman calls | Sanger calls | Pearson Correlation |
| rs5743890 | 148 | 149 | 1 |
| rs5743894 | 147 | 154 | 0.99 |
| rs3750920 | 151 | 153 | 1 |
| rs5743854 | 154 | 154 | 0.81 |
| rs35705950 | 149 | 154 | 0.98 |

Genotypes for those in the INSPIRE cohort were conducted using the iPLEX Gold™ Platform following manufacturer's protocol (Sequenom, San Diego, Calif.), while UC cohort was subjected to custom-designed target capture the Agilent SureSelect XT2 kit followed by manufacturer's protocols. Paired-end reads of 100 bases were generated on HiSeq2000. Data analysis was performed by the Center for Research Informatics at University of Chicago using a modified Illumina's Exome pipeline, including SeqPrep, FastQC, NovoAlign, Picard, SAMtools, GATK2, and Annovar.

Statistical Analysis:

Continuous variables are reported as means with standard deviation (SD) and are compared using a Student's t-test or one-way analysis of variance, as appropriate. Categorical variables are reported as counts and percentages and compared using a Chi-square or Fisher's exact test, as appropriate. SNP correlation was determined using Pearson's correlation coefficient. Survival analysis was conducted using an unadjusted logrank test and multivariable Cox proportional hazards modeling and plotted using the Kaplan-Meier survival estimator.

The primary analysis tested whether statistical interaction was present between SNPs of interest and NAC therapy with regard to composite endpoint-free survival, defined as time from trial enrollment to death, ≥10% FVC decline, hospitalization or transplantation. Interaction was formally tested with a multivariable Cox regression model that included the following variables: SNP genotype, NAC therapy, and a SNP*NAC interaction term, age, gender, FVC (% predicted) and DLCO (% predicted). Statistical interaction was considered present when the Wald z-statistic for SNP*NAC interaction term corresponded to a p-value <0.01, which adjusts for multiple testing by Bonferroni correction. Interaction detected by this method was then further explored by constructing genotype-stratified multivariable Cox models to determine genotype-specific endpoint risk associated with NAC therapy. Based on SNP distributions, an additive allelic model was assumed for rs3750920 (TOLLIP) and a dominant model for rs5743890 (TOLLIP), rs5743894 (TOLLIP), rs5743854 (TOLLIP) and rs35705950 (MUC5B). Each model was checked to ensure that the proportional hazards assumption was met.

Hospitalization data were not available for patients in the replication cohort so composite endpoint-free survival was defined as time from trial enrollment (INSPIRE) or blood draw (UChicago) to death, ≥10% FVC decline or transplantation in those not receiving NAC therapy and time from NAC initiation to death, >10% FVC decline or transplantation in those receiving NAC therapy. Because follow-up time was longer for the UChicago compared to INSPIRE cohort, UChicago cohort survival time was censored at 170 weeks to allow for merging of the datasets. All statistical analysis was conducted using Stata (StataCorp. 2011. Release 12. College Station, Tex.).

Results

Figure 2:
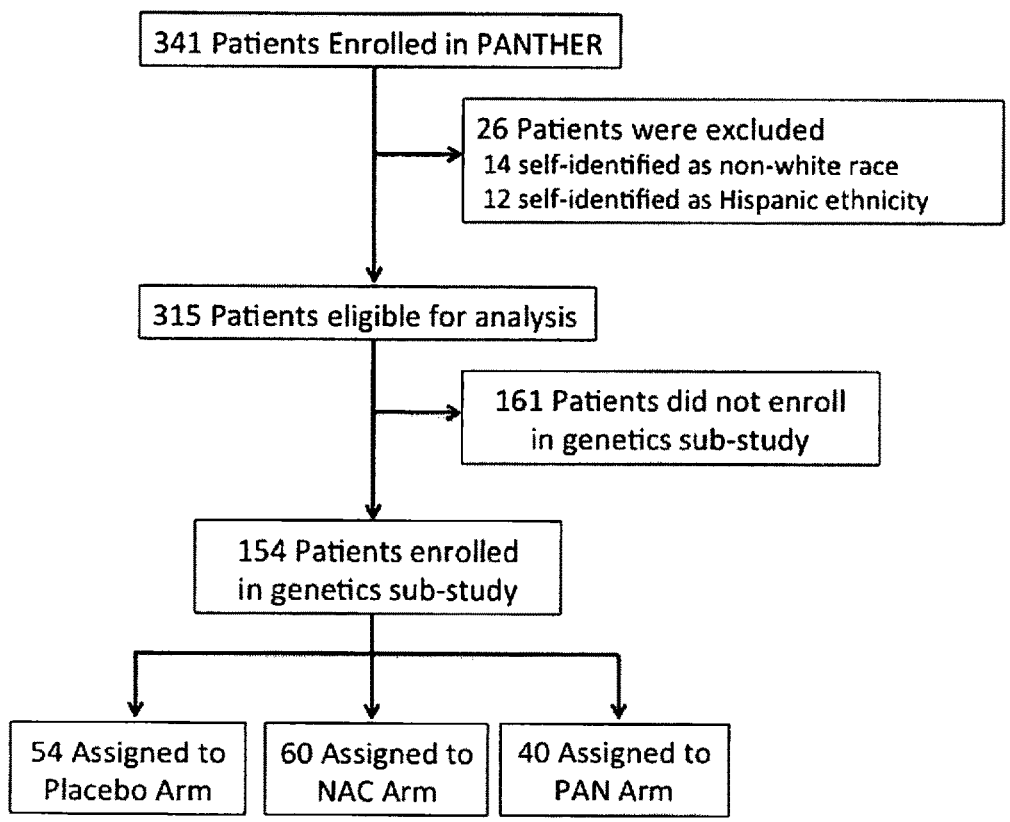
FIG. 2 shows the PANTHER consort diagram, and is further described in Example 1.

PANTHER Cohort:

Of the 341 patients enrolled in the PANTHER trial, 315 self-reported a non-Hispanic white ethnicity (FIG. 2). Of those 315 individuals, 154 consented to genetic testing and were included in the primary analysis. Among genotyped patients, fifty-four patients received placebo therapy and sixty patients received NAC therapy. Baseline demographic and clinical characteristics between non-Hispanic white genotyped (n=154) and non-genotyped (n=161) patients stratified by treatment group are shown in Table 1.

TABLE 1

PANTHER Baseline Characteristics and Genotypes*

| | Genotyped (n = 154) | | Non-Genotyped (n = 161) | | |
|---|---|---|---|---|---|
| Characteristic | Placebo Arm (n = 54) | NAC Arm (n = 60) | Placebo Arm (n = 66) | NAC Arm (n = 61) | p-value |
| Age, mean (±SD) | 66.1 (7.9) | 67.9 (8.7) | 66.8 (8.2) | 67.8 (8.2) | 0.62 |
| Male, n (%) | 39 (72.2) | 47 (78.3) | 53 (80.3) | 51 (83.6) | 0.5 |
| Ever Smoker, n (%) | 41 (75.9) | 44 (73.3) | 50 (75.8) | 46 (76.7) | 0.98 |
| FVC, % predicted (±SD) | 73.2 (14.7) | 73 (15.7) | 74 (13.8) | 73 (15.8) | 0.98 |
| DLCO, % predicted (±SD) | 46.4 (11.7) | 43.9 (10.9) | 44.7 (12.1) | 46.2 (10.8) | 0.59 |
| Death, n (%) | 2 (3.7) | 1 (1.7) | 1 (1.5) | 3 (4.9) | 0.64 |
| FVC Decline ≥ 10%, n (%) | 12 (22.2) | 11 (18.3) | 17 (25.8) | 17 (27.9) | 0.62 |
| Hospitalization, n (%) | 8 (14.8) | 8 (13.3) | 10 (15.2) | 9 (14.8) | 0.99 |
| Transplant, n (%) | 1 (1.9) | 3 (5) | 1 (1.5) | 1 (1.6) | 0.67 |
| Composite Endpoint**, n (%) | 17 (31.5) | 19 (31.7) | 24 (36.4) | 26 (42.6) | 0.55 |
| SNP (Gene) Genotype, count (%) | | | | | |
| rs5743890 (TOLLIP) AA/AG/GG | 43/10/0 0.81/0.19/0 | 52/8/0 0.87/0.13/0 | — | — | 0.42 |
| rs5743894 (TOLLIP) AA/AG/GG | 29/21/4 0.54/0.39/0.07 | 31/25/4 0.52/0.42/0.06 | — | — | 0.96 |
| rs3750920 (TOLLIP) CC/CT/TT | 14/23/17 0.26/0.43/0.31 | 13/30/16 0.22/0.51/0.27 | — | — | 0.68 |
| rs5743854 (TOLLIP) CC/CG/GG | 44/10/0 0.81/0.19/0 | 55/5/0 0.92/0.08/0 | | | 0.09 |
| rs35705950 (MUC5B) GG/GT/TT | 20/29/5 0.37/0.54/0.09 | 14/42/4 0.23/0.7/0.07 | — | — | 0.19 |

Abbreviations:
NAC = N-acetylcysteine;
FVC = forced vital capacity;
DLCO = diffusion capacity for carbon monoxide
*Non-Hispanic white individuals by self-report
**Death, 10% FVC decline, hospitalization or transplantation No differences were observed between genotyped and non-genotyped individuals with regard to age, gender, smoking history and pulmonary function. Trial endpoints, including death, FVC decline ≥10%, hospitalization and lung transplantation, as well as the composite endpoint, were similar between genotyped and non-genotyped individuals. SNP genotype counts (Table 1) were similar between treatment groups.

When considering patients enrolled prior to and following the clinical alert, a non-statistically significant imbalance in genotype frequencies was observed between the placebo and NAC arms with regard to rs5743894 (TOLLIP) (p=0.17), rs3750920 (TOLLIP) (p=0.12) and rs35705950 (MUC5B) (p=0.08) (Table 2).

TABLE 2

Treatment-stratified SNP Comparison Before and After PANTHER Clinical Alert

| | Before Clinical Alert | | | After Clinical Alert | | |
|---|---|---|---|---|---|---|
| SNP (Gene), Genotype | Placebo Arm | NAC Arm | p-value | Placebo Arm | NAC Arm | p-value |
| rs5743890 AA/AG/GG | 25/5/0 (0.83/0.17/0) | 41/7/0 (0.85/0.15/0) | 0.80 | 18/5/0 (0.78/0.22/0) | 11/1/0 (0.92/0.08/0) | 0.64 |
| rs5743894 AA/AG/GG | 14/14/3 (0.45/0.45/0.10) | 27/18/3 (0.56/0.38/0.06) | 0.64 | 15/7/1 (0.65/0.30/0.05) | 4/7/1 (0.33/0.59/0.08) | 0.17 |
| rs3750920 CC/CT/TT | 6/16/9 (0.19/0.52/0.29) | 10/22/15 (0.21/0.47/0.32) | 0.92 | 8/7/8 (0.35/0.30/0.35) | 3/8/1 (0.25/0.67/0.08) | 0.12 |
| rs5743854 CC/CG/GG | 26/5/0 0.84/0.16/0 | 44/4/0 0.92/0.08/0 | 0.3 | 18/5/0 0.78/0.22/0 | 11/1/0 0.92/0.08/0 | 0.64 |
| rs35705950 GG/GT/TT | 11/16/4 (0.35/0.52/0.13) | 13/31/4 (0.27/0.65/0.08) | 0.54 | 9/13/1 (0.39/0.57/0.04) | 1/11/0 (0.08/0.92/0) | 0.08 |

Abbreviations:
SNP = single nucleotide polymorphism;
NAC = N-acetylcysteine;
PAN = prednisone/azathioprine/N-acetylcysteine Minor allele frequencies (MAF) were compared between PANTHER participants and those comprising the GWAS stage 2 replication cohort in reference 1. Groups were compared by multiplying the total number of patients in each cohort by the MAF and conducting a Chi-square test, which compared the expected and observed major and minor alleles in each cohort. This is shown in Table 3:

TABLE 3

Minor Allele Frequency Comparison Between PANTHER and GWAS Cohorts

| SNP_minor allele (Gene) | n | PANTHER MAF | GWAS MAF* | p-value |
|---|---|---|---|---|
| rs5743890_G (TOLLIP) | 149 | 0.08 | 0.09 | 0.61 |
| rs5743894_G (TOLLIP) | 154 | 0.29 | 0.24 | 0.08 |
| rs3750920_T (TOLLIP) | 153 | 0.53 | 0.5 | 0.31 |
| rs5743854_G (TOLLIP)** | 154 | 0.06 | — | — |
| rs35705950_T (MUC5B) | 154 | 0.4 | 0.33 | 0.02 |

Abbreviations:
SNP = single nucleotide polymorphism;
MAF = minor allele frequency
*Based on GWAS Stage 2 replication cohort in reference 1
**GWAS data not available When comparing the minor allele frequency (MAF) for each SNP between the PANTHER cohort and a recent GWAS[1] stage II replication cohort (Table 3), the MAF of rs35705950_T (MUC5B) was significantly higher in the PANTHER cohort compared to the GWAS cohort (0.4 vs 0.33, respectively; p=0.02). The MAF of rs5743894_G (TOLLIP) was also higher in the PANTHER cohort compared to the GWAS cohort (0.29 vs 0.24, respectively), but this difference was not statistically significant (p=0.08). No SNPs were in strong linkage disequilibrium based on methodology outlined above, nor were any significantly correlated in the PANTHER dataset (Table 4). Pairwise correlation was conducted using the SNP annotation and proxy search program (SNAP) with 1000 genomes project data (references 19, 20). PANTHER SNPs were then correlated using Pearson correlation.

TABLE 4

Pairwise SNP correlation

| SNP 1 | SNP 2 | Rsquared* | Dprime* | PANTHER** |
|---|---|---|---|---|
| rs5743890 (TOLLIP) | rs5743894 (TOLLIP) | 0.028 | 1 | −0.1 |
| rs5743890 (TOLLIP) | rs3750920 (TOLLIP) | 0.058 | 0.58 | 0.22 |
| rs5743890 (TOLLIP) | rs5743854 (TOLLIP) | 0.019 | 1 | 0.01 |
| rs5743890 (TOLLIP) | rs35705950 (MUC5B) | 0.009 | 0.786 | −0.21 |
| rs5743894 (TOLLIP) | rs3750920 (TOLLIP) | 0.078 | 0.532 | 0.49 |
| rs5743894 (TOLLIP) | rs5743854 (TOLLIP) | 0.03 | 1 | −0.23 |
| rs5743894 (TOLLIP) | rs35705950 (MUC5B) | 0.158 | 0.549 | 0.52 |
| rs5743854 (TOLLIP) | rs35705950 (MUC5B) | 0 | 0 | −0.26 |
| rs3750920 (TOLLIP) | rs35705950 (MUC5B) | 0.084 | 0.761 | 0.48 |

*Based on SNAP analysis using 1000 Genomes Project (references 19, 20)
**Based on Pearson correlation Survival modeling shows that no SNP independently predicted composite endpoint-free survival in multivariable Cox regression adjusting for treatment arm assignment, age, gender, FVC (% predicted) and DLCO (% predicted) (Table 5). Using a multivariable Cox regression model adjusting for treatment arm and GAP score (based on reference 17), no SNP was an independent predictor of endpoint risk in either progression-free survival or hospitalization-free survival.

TABLE 5

Composite Endpoint Risk Associated with TOLLIP and MUC5B SNPs

| SNP (Gene), allele | Reference Allele | HR | p-value | 95% CI |
|---|---|---|---|---|
| rs5743890 (TOLLIP), G | A | 1.06 | 0.88 | 0.52-2.15 |
| rs5743894 (TOLLIP), G | A | 0.8 | 0.43 | 0.46-1.38 |
| rs3750920 (TOLLIP), T | C | 0.93 | 0.74 | 0.62-1.40 |
| rs5743854 (TOLLIP), G** | C | 0.87 | 0.76 | 0.36-2.10 |
| rs35705950 (MUC5B), T | G | 1.14 | 0.66 | 0.63-2.09 |

*Adjusted for treatment arm assignment, age, gender, FVC and DLCO
**This SNP did not meet the proportional hazards assumption in this model so was omitted from subsequent analyses The proportional hazards assumption for rs5743854 was not met in this modeling so this SNP was omitted from subsequent analyses. Multivariable Cox interaction modeling (Table 6) showed significant interaction between NAC therapy and the T allele of rs3750920 within TOLLIP ($p_{interaction}$=0.002). A suggestion of potential interaction was observed between NAC therapy and the T allele of rs35705950 (MUC5B) ($p_{interaction}$=0.06) and the G allele of rs5743894 (TOLLIP) ($p_{interaction}$=0.05). No SNP modified endpoint risk among those receiving placebo therapy.

Interaction is statistically significant when SNP*treatment interaction term has p-value <0.01, based on Bonferroni correction for multiple testing.

TABLE 6

Multivariable Cox Interaction Model Estimates*

| Variable | Coefficient (95% CI) | p-value |
|---|---|---|
| rs5743890 (TOLLIP) | 0.84 (−0.32-1.99) | 0.16 |
| NAC Therapy | 0.17 (−0.58-0.92) | 0.66 |
| PAN Therapy | 1.36 (0.56-2.17) | 0.001 |
| rs5743890*NAC interaction | −1.17 (−2.91-0.56) | 0.19 |
| rs5743890*PAN interaction | −1.08 (−2.70-0.55) | 0.19 |
| rs5743894 (TOLLIP) | 0.05 (−0.91-1.00) | 0.93 |
| NAC Therapy | 0.45 (−0.40-1.30) | 0.30 |
| PAN Therapy | 0.74 (−0.30-1.78) | 0.17 |
| rs5743894*NAC interaction | −1.42 (−2.89-0.06) | 0.06 |

TABLE 6-continued

Multivariable Cox Interaction Model Estimates*

| Variable | Coefficient (95% CI) | p-value |
|---|---|---|
| rs5743894*PAN interaction | 0.58 (−0.82-1.97) | 0.42 |
| rs3750920 (TOLLIP) | 0.39 (−0.32-1.10) | 0.28 |
| NAC Therapy | 1.34 (0.17-2.52) | 0.03 |

TABLE 6-continued

Multivariable Cox Interaction Model Estimates*

| Variable | Coefficient (95% CI) | p-value |
|---|---|---|
| PAN Therapy | 0.89 (−0.49-2.27) | 0.20 |
| rs3750920*NAC interaction | −1.47 (−2.45−−0.48) | 0.004 |
| rs3750920*PAN interaction | 0.19 (−0.81-1.19) | 0.71 |
| rs35705950 (MUC5B) | 0.61 (−0.53-1.75) | 0.29 |
| NAC Therapy | 0.91 (−0.34-2.51) | 0.15 |
| PAN Therapy | 0.98 (−0.42-2.37) | 0.17 |
| rs35705950*NAC interaction | −1.40 (−2.89-0.09) | 0.07 |
| rs35705950*PAN interaction | 0.13 (−1.48-1.74) | 0.87 |

*Adjusted for age, gender, FVC and DLCO

Figure 4:
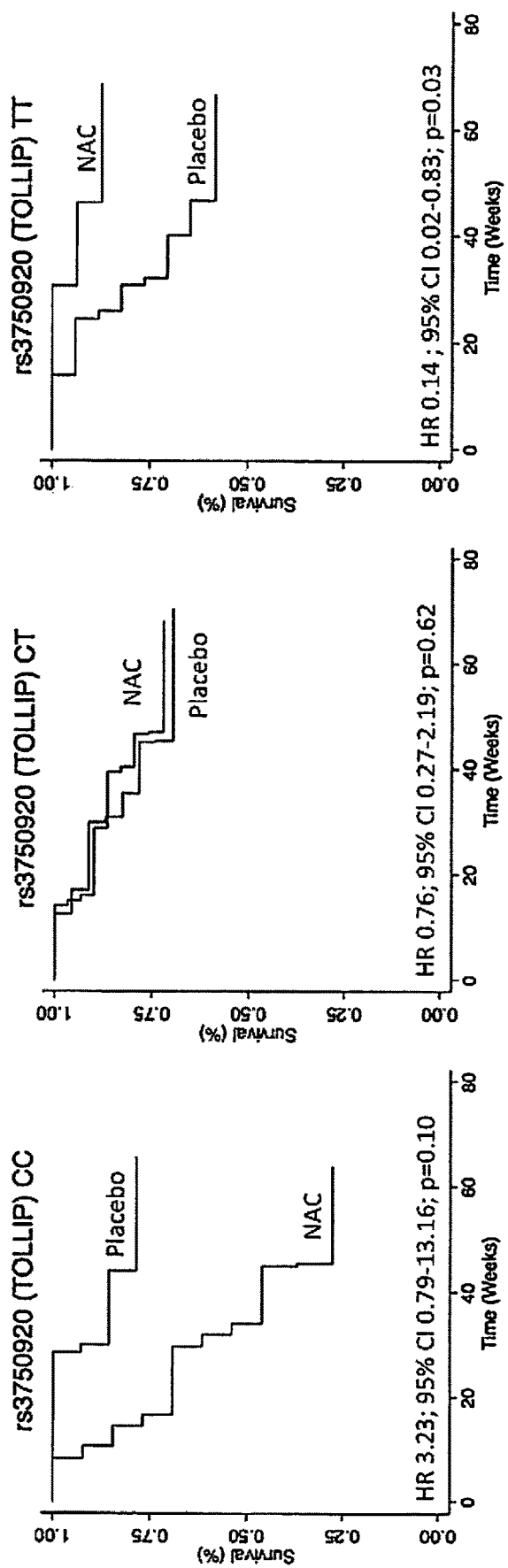
FIG. 4 shows endpoint-free survival between NAC and Placebo groups in the PANTHER clinical trial after stratification by rs3750920 (TOLLIP) genotype.

After stratifying by rs3750920 (TOLLIP) genotype (FIG. 4), compared to placebo, the composite endpoint risk associated with NAC therapy was significantly reduced among those with a TT genotype (HR 0.14; 95% CI 0.02-0.83; p=0.03). A non-significant reduction in composite endpoint risk was observed among those with a CT genotype (HR 0.76; 95% CI 0.27-2.19; p=0.62) and non-significant increase in composite endpoint risk was observed among those with a CC genotype (HR 3.23; 95% CI 0.79-13.16; p=0.10).

Given the potential interaction observed between NAC therapy and rs5743894 within TOLLIP and rs35705950 within MUC5B, a sensitivity analysis (Table 7) was conducted for these SNPs, along with the rs3750920 (TOLLIP), to determine whether individual SNP genotypes predicted specific endpoints. Along with our primary composite endpoint, we assessed hospitalization-free survival, defined as time to death, hospitalization or transplant, and progression-free survival, defined as time to death, 10% FVC decline or transplant. Death and transplant were not considered in isolation, as there were not enough events for robust analysis.

TABLE 7

Sensitivity Analysis of NAC-associated endpoint risk after rs3750920, rs5743894 and rs35705950 stratification*

| SNP Genotype (Gene) | Primary Composite Endpoint | | Hospitalization-Free Survival | | Progression-Free Survival | |
|---|---|---|---|---|---|---|
| | HR (95% CI) | p-value | HR (95% CI) | p-value | HR (95% CI) | p-value |
| rs3750920 (TOLLIP) CC | 3.22 (0.79-13.16) | 0.1 | 3.74 (0.35-39.80) | 0.27 | 1.27 (0.21-7.55) | 0.79 |
| rs3750920 (TOLLIP) CT | 0.76 (0.27-2.19) | 0.62 | 0.45 (0.10-2.15) | 0.32 | 0.63 (0.17-2.30) | 0.48 |
| rs3750920 (TOLLIP) TT | 0.14 (0.02-0.83) | 0.03 | ** | ** | 0.09 (0.01-0.76) | 0.03 |
| rs5743894 (TOLLIP) AA | 1.67 (0.71-3.95) | 0.24 | 1.43 (0.44-4.70) | 0.56 | 1.68 (0.58-4.90) | 0.34 |
| rs5743894 (TOLLIP) AG/GG | 0.33 (0.10-1.14) | 0.08 | 0.21 (0.02-1.99) | 0.18 | 0.18 (0.04-0.90) | 0.04 |
| rs35705950 (MUC5B) GG | 2.02 (0.57-7.20) | 0.28 | 1.25 (0.15-10.30) | 0.84 | 3.72 (0.69-20.16) | 0.13 |
| rs35705950 (MUC5B) GG/TT | 0.60 (0.27-1.35) | 0.22 | 0.49 (0.15-1.58) | 0.23 | 0.32 (0.11-0.94) | 0.04 |

* Models adjusted for age, gender, FVC (% predicted) and DLCO (% predicted)

** No events observed in this group so HR could not be estimated

Primary Composite Endpoint = death, hospitalization, 10% FVC decline or transplant Progression-Free Survival = death, 10% FVC decline or transplant Hospitalization-Free Survival = death, hospitalization or transplant This analysis showed that when compared to placebo, a consistent hazard reduction occurred in patients receiving NAC therapy with each T allele of rs3750920 (TOLLIP) with regard to all three endpoints. It also showed that NAC recipients had a significant reduction in endpoint risk when considering progression-free survival with an rs5743894 (TOLLIP) AG/GG genotype (HR 0.18; 95% CI 0.04-0.90; p=0.04) and rs35705950 (MUC5B) GT/TT genotype (HR 0.32; 95% CI 0.11-0.94; p=0.04).

Replication Cohort:

Based on the findings above, interaction modeling was performed in an independent cohort between NAC therapy and rs3750920 (TOLLIP), rs5743894 (TOLLIP) and rs35705950 (MUC5B). Of the 771 non-Hispanic white individuals enrolled in the INSPIRE trial, DNA was available for 314. In the UChicago cohort, of 151 non-Hispanic white individuals with sequencing data, 91 had longitudinal PFT data and were included in the analysis. A summary of baseline demographic and clinical characteristics, along with genotype counts for the INSPIRE, UChicago and combined cohorts are shown in Table 8.

($p_{interaction}$=0.005). No interaction was observed between NAC therapy and rs5743894 (TOLLIP) ($p_{interaction}$=0.41).

TABLE 9

Replication Cohort Multivariate Cox Interaction Model Estimates

| Variable | Coefficient (95% CI) | p-value |
|---|---|---|
| rsrs5743894 (TOLLIP) | −0.07 (−0.35-0.22) | 0.67 |
| NAC Therapy | 0.54 (0.01-1.07) | 0.05 |
| rs3750920*NAC interaction | −0.40 (−1.33-0.54) | 0.41 |
| rs3750920 (TOLLIP) | −0.07 (−0.22-0.2) | 0.95 |
| NAC Therapy | 1.37 (0.69-2.05) | <0.001 |
| rs3750920*NAC interaction | −0.86 (−1.43--0.29) | 0.003 |
| rs35705950 (MUC5B) | −0.17 (−0.49-0.15) | 0.31 |
| NAC Therapy | 1.24 (0.58-1.90) | <0.001 |
| rs35705950*NAC interaction | −1.30 (−2.20--0.39) | 0.005 |

*Adjusted for age, gender, FVC and DLCO, prednisone use, azathioprine use and study cohort Table 10 shows rs3750920 (TOLLIP) and rs35705950 (MUC5B) genotype-stratified composite endpoint risk asso-

TABLE 8

Replication Cohort Baseline Characteristics and Genotypes*

| | INSPIRE (n = 314) | | UChicago (n = 91) | | Combined Cohort (n = 405) | | |
|---|---|---|---|---|---|---|---|
| Characteristic | NAC (n = 29) | Non-NAC (n = 285) | NAC (n = 18) | Non-NAC (n = 73) | NAC (n = 47) | Non-NAC (n = 358) | p-value |
| Age, mean (±SD) | 65.8 (7.5) | 66.2 (7.7) | 72.4 (8.0) | 67.3 (8.1) | 68.3 (8.3) | 66.4 (7.8) | 0.12 |
| Male, n (%) | 18 (62.1) | 210 (73.7) | 15 (83.3) | 57 (78.1) | 33 (70.2) | 267 (74.6) | 0.52 |
| Ever Smoker, n (%) | 18 (62.1) | 199 (69.8) | 15 (83.3) | 36 (73.5) | 33 (70.2) | 235 (70.4) | 0.98 |
| Azathioprine therapy, n (%) | 4 (13.8) | 9 (3.2) | 1 (5.9) | 1 (1.4) | 5 (10.9) | 10 (2.8) | 0.02 |
| Prednisone therapy, n (%) | 19 (65.5) | 121 (42.5) | 4 (23.5) | 11 (15.1) | 23 (50.0) | 132 (36.9) | 0.09 |
| FVC, % predicted (±SD) | 72.3 (11.9) | 71.3 (12.6) | 58.9 (15.0) | 70.3 (19.4) | 67.3 (14.5) | 71.1 (14.2) | 0.09 |
| DLCO, % predicted (±SD) | 47.9 (8.4) | 47.3 (9.2) | 37 (10.8) | 50.7 (19.1) | 44.0 (10.6) | 48.0 (11.9) | 0.03 |
| Death, n (%) | 6 (20.7) | 49 (17.2) | 13 (72.2) | 29 (39.7) | 19 (40.4) | 78 (21.8) | 0.01 |
| FVC Decline ≥10%, n (%) | 13 (44.8) | 115 (40.4) | 4 (22.2) | 17 (23.3) | 17 (36.2) | 132 (36.9) | 0.93 |
| Transplant, n (%) | 2 (6.9) | 4 (1.4) | 0 (0) | 7 (9.6) | 2 (4.3) | 11 (3.1) | 0.46 |
| Composite Endpoint**, n (%) | 14 (48.3) | 146 (51.2) | 13 (72.2) | 45 (61.6) | 27 (57.5) | 167 (46.7) | 0.6 |
| SNP (Gene) Genotype, count (%) | | | | | | | |
| rs5743894 (TOLLIP) | 18/11/0 | 143/129/14 | 11/8/2 | 60/31/10 | 29/16/2 | 188/151/19 | 0.53 |
| AA/AG/GG | 0.62/0.38/0 | 0.5/0.45/0.05 | 0.52/0.38/0.1 | 0.59/0.31/0.1 | 0.62/0.34/0.04 | 0.53/0.42/0.05 | |
| rs3750920 (TOLLIP) | 6/15/8 | 61/157/66 | 3/12/6 | 21/49/31 | 9/25/13 | 77/194/86 | 0.84 |
| CC/CT/TT | 0.21/0.52/0.27 | 0.22/0.55/0.23 | 0.14/0.57/0.29 | 0.21/0.48/0.31 | 0.19/0.53/0.28 | 0.22/0.54/0.24 | |
| rs35705950 (MUC5B) | 10/16/3 | 82/185/15 | 8/13/0 | 31/62/8 | 17/27/3 | 105/230/20 | 0.57 |
| GG/GT/TT | 0.35/0.55/0.1 | 0.29/0.66/0.05 | 0.38/0.62/0 | 0.31/0.61/0.08 | 0.36/0.57/0.07 | 0.30/0.65/0.05 | |

Abbreviations:
NAC = N-acetylcysteine;
PAN = prednisone/azathioprine/N-acetylcysteine;
FVC = forced vital capacity;
DLCO = diffusion capacity for carbon monoxide
*Non-Hispanic white individuals by self-report
**Death, 10% FVC decline, hospitalization or transplantation Those in the UChicago cohort tended to have poorer lung function and an increased number of deaths and composite endpoint events compared to the INSPIRE cohort. After combining cohorts, compared to those who did not receive NAC therapy, those receiving NAC therapy had increased concurrent azathioprine use (2.8% vs 10.9%; respectively p=0.02) and were sicker overall with worse DLCO (48% predicted vs 44% predicted, respectively; p=0.03) and more deaths (21.8% vs 40.4%, respectively; p=0.01). There was no difference in genotype counts between groups.

Multivariable Cox interaction models (Table 9) showed significant interaction between NAC therapy and rs3750920 (TOLLIP) ($p_{interaction}$=0.003) and rs35705950 (MUC5B)

ciated with NAC therapy after adjustment for age, gender, FVC (% predicted) and DLCO (% predicted).

TABLE 10

Replication Cohort Genotype-stratified Composite Endpoint Risk Associated with NAC Therapy

| Genotype | HR | 95% CI | p-value |
|---|---|---|---|
| rs3750920 (TOLLIP) CC | 3.51 | 1.44-8.56 | 0.01 |
| rs3750920 (TOLLIP) CT | 2.27 | 1.19-4.31 | 0.01 |
| rs3750920 (TOLLIP) TT | 0.23 | 0.06-0.93 | 0.04 |
| rs35705950 (MUC5B) GG | 3.15 | 1.47-6.72 | 0.003 |

TABLE 10-continued

Replication Cohort Genotype-stratified Composite
Endpoint Risk Associated with NAC Therapy

| Genotype | HR | 95% CI | p-value |
|---|---|---|---|
| rs35705950 (MUC5B) GT/TT | 0.94 | 0.50-1.76 | 0.84 |

Figure 3:
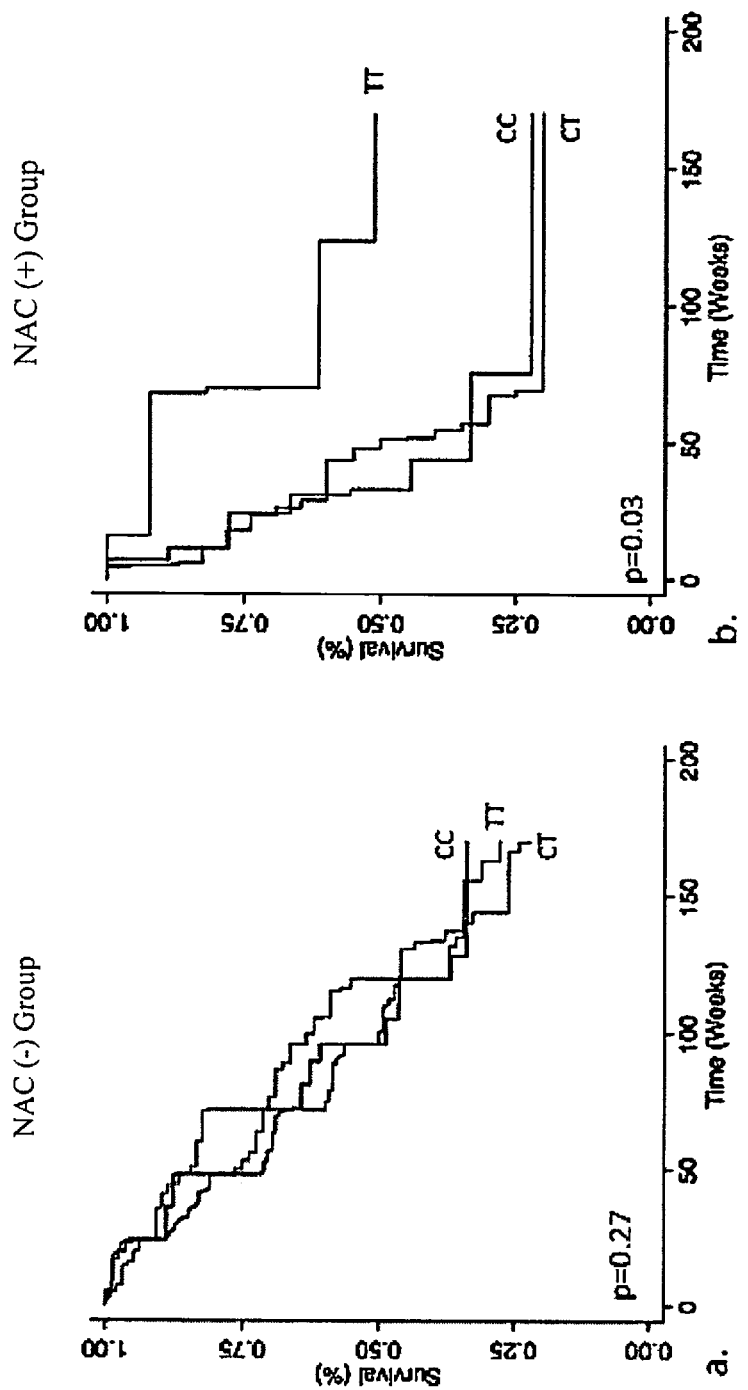
FIGS. 3A-B shows replication cohort rs3750920 genotype-stratified Kaplan-Meier survival curves between those who did and did not receive NAC therapy. Whereas rs3750920 genotype was not associated with survival in those who did not receive NAC therapy (a), a TT genotype in those receiving NAC therapy (b) was associated with significantly better survival than those with a CC or CT genotype.

Compared to those who did not receive NAC therapy, the composite endpoint risk associated with NAC therapy was significantly reduced among those with a rs3750920 (TOLLIP) TT genotype (HR 0.23; 95% CI 0.06-0.93; p=0.04) but significantly increased among those with a CT genotype (HR 2.27; 95% CI 1.19-4.31; p=0.01) and CC genotype (HR 3.51; 95% CI 1.44-8.56; p=0.01). Unadjusted endpoint-free survival between those who did and did not receive NAC therapy stratified by rs3750920 (TOLLIP) genotype is shown in FIG. 3. While genotype was not associated with outcome in those who did not receive NAC (p=0.27), among NAC recipients those with an rs3750920 (TOLLIP) TT genotype demonstrated significantly better overall survival compared to those with CT and CC genotypes (p=0.03). With regard to rs35705950 (MUC5B), compared to those who did not receive NAC therapy, the composite endpoint risk associated with NAC therapy was significantly increased in those with a GG genotype (HR 3.15; 95% CI 1.47-6.72; p=0.003) but no different in those with a GT or TT genotype (HR 0.94; 95% CI 0.5-1.76; p=0.84).

Discussion

In this study, Applicants showed that polymorphisms within TOLLIP and MUC5B may influence the response to NAC therapy in patients with IPF. This represents the first significant drug-gene interaction observed in patients with IPF. Whereas PANTHER investigators previously reported that NAC therapy did not provide benefit for patients with IPF, Applicants demonstrate here that NAC therapy may reduce clinically meaningful endpoint risk for genetically predisposed individuals, specifically those carrying an rs3750920 (TOLLIP) TT genotype. As this genotype is found in approximately 25% of patients with IPF, those who may benefit from NAC therapy represent a significant minority of patients. Discordant results between the PANTHER and replication cohorts make the clinical significance of a CT genotype unclear, but the potential harm observed among NAC recipients with a CC genotype should give pause to those using off-label NAC to treat IPF.

The potential role of the rs5743894 (TOLLIP) and rs35705950 (MUC5B) polymorphisms in modifying the effect of NAC therapy also remains unclear. The minor allele of both these SNPs was associated with significantly improved progression-free survival in the PANTHER cohort, but these results could not be replicated. One potential reason for this lies in the fact that NAC recipients in the replication cohort had significantly worse pulmonary function compared to those who did not receive NAC, potentially limiting the ability to detect drug-gene interaction in patients with advanced disease. This may also explain the discordant results between cohorts with regard to the rs3750920 (TOLLIP) CT genotype. Concurrent prednisone (50%) and azathioprine (10%) usage among NAC recipients in the replication cohort may have also influenced these findings, as these therapies increase the risk of death and hospitalization in patients with IPF. An insufficient number of individuals received NAC monotherapy in the replication cohort to conduct robust analysis with this group alone.

The biology underpinning an interaction between NAC therapy and polymorphisms within TOLLIP and MUC5B may lie in lung host defense. TOLLIP encodes the Toll-interacting protein (TOLLIP), which is a negative inhibitor of toll-like receptors (TLRs), including TLR2 and TLR4, and may play a key role in the innate immune response to lung injury. This TLR-mediated inflammatory response is oxidant dependent in some cases and can be blocked by the presence of NAC. Polymorphisms in TOLLIP, including rs3750920, have been linked to decreased TOLLIP mRNA production, raising the question of whether decreased TOLLIP expression allows for unmitigated TLR2 and TLR4 activity, the harmful effects of which may be reduced with antioxidant therapy.

MUC5B also plays a critical role in airway defense. Reduced MUC5B expression has been linked to impaired airway mucociliary clearance and chronic bacterial infection, whereas increased expression, which occurs with the rs35705950 polymorphism, has been linked to improved host defense. The mechanism by which lower airway bacterial colonization occurs in patients with IPF remains unclear, but the presence of specific genera, including *Staphylococcus*, along with a high bacterial burden, has been associated with reduced survival in IPF. Those carrying the rs35705950 polymorphism have been shown to have lower bacterial burden, potentially explaining the improved survival among those with this SNP. NAC can reduce biofilm formation and enhance intracellular killing of *Staphylococcus*, which may further enhance airway host defense in the presence of the rs35705950 polymorphism. The discordant results between the PANTHER and replication cohorts indicate that this beneficial interaction may be limited to those with mild-to-moderate disease.

Despite the novel findings of this investigation, it had several limitations. First, adjustments for genetic ancestry was not possible as race/ethnicity was self-reported. Second, less than 50% of participants consented to genetic analysis in the PANTHER cohort, thus limiting the power of this analysis and leaving it unclear whether our results would be consistent throughout the entire cohort. No systematic baseline or endpoint differences were observed between genotyped and non-genotyped patients and while composite endpoint risk associated with NAC therapy was somewhat lower in genotyped compared to non-genotyped patients (Table 11), these estimates were not statistically significant. Replication of these findings also helps assure this finding is not unique to the PANTHER dataset. Another issue arising from the small sample size was the inability to use the additive allelic model for each SNP. An additive model may better characterize the dose-dependent nature of gene polymorphisms and has been used to model genotypes in previous IPF genetic and genomic investigations.

TABLE 11

Treatment-Specific Composite Endpoint Risk* Between Genotyped and Non-genotyped Patients in the PANTHER Trial

| | Genotyped | | | Non-Genotyped | | |
|---|---|---|---|---|---|---|
| Intervention | HR | p-value | 95% CI | HR | p-value | 95% CI |
| NAC Therapy | 0.92 | 0.81 | 0.48-1.79 | 1.31 | 0.35 | 0.74-2.32 |
| PAN Therapy | 2.87 | 0.002 | 1.46-5.64 | 1.45 | 0.33 | 0.68-3.08 |

*Adjusted for age, gender, FVC (% predicted) and DLCO (% predicted)

In conclusion, NAC may be an effective therapy for genetically susceptible individuals with IPF. Further research is needed, by way of a randomized clinical trial, to delineate better the clinical implications of this drug-gene interaction. These findings highlight the importance of pharmacogenomics in IPF clinical trials and strongly support an effort to systematically acquire biospecimens on all patients participating in IPF clinical trials. Such practice may not only identify genetic subgroups likely to benefit from a particular therapy, but spare others significant side effects and adverse events.

Example 2: Genetic Heterogeneity Among Patients Enrolled in the Panther-IPF Clinical Trial Rationale: Idiopathic pulmonary fibrosis (IPF) is a deadly fibrosing interstitial lung disease of unknown cause. Recent genome-wide association studies (GWAS) have identified single nucleotide polymorphisms (SNPs) linked to disease risk as well as mortality. Genetic determinants of clinically relevant outcomes, including mortality and disease progression have not been investigated in IPF clinical trials to date. In this study, Applicants compare genetic profiles of patients enrolled in the PANTHER-IPF clinical trial to a recent GWAS and determine whether disease-associated SNPs were balanced among treatment arms.

Methods: Genotypes of 5 SNPs on Chr11-rs35705950 in MUC5B and rs5743890, rs5744034, rs3750920, and rs5743854 in TOLLIP—were analyzed in 165 PANTHER participants who consented to a genetics sub-study. The minor allele frequency (MAF) of each SNP was compared to that of 868 IPF GWAS patients. Minor allele counts were then compared between the prednisone/azathioprine/N-acetylcysteine (PAN), N-acetylcysteine (NAC) and placebo arms with observed MAF in each arm used to impute genotypes for the remainder of the cohort. Cox regression was performed to determine whether SNPs influenced composite endpoint (death, hospitalization, 10% FVC decline) risk in genotyped patients.

Results: The MAFs of two SNPs were significantly different between patients enrolled in PANTHER and GWAS-rs35705950 (0.4 vs. 0.32, respectively; p=0.01) and rs5744034 (0.28 vs. 0.22, respectively; p=0.02). There were fewer minor alleles of rs5743854 in the PAN vs. placebo arms (3 vs. 9, respectively; p=0.04) and after imputing genotypes to the remaining cohort, more minor alleles of rs35705950 (56 vs 45, respectively; p=0.05) and fewer of rs5743854 (6 vs 17, respectively; p=0.01) were observed. Similar results with regard to rs35705950 and rs5743854 were found in the NAC vs. placebo arms along with more minor alleles of rs3750920 (91 vs 78 respectively; p=0.02). No SNP was an independent predictor of composite endpoint risk but the minor allele of rs3750920 did modify the risk associated with PAN therapy (Table 12).

TABLE 12

| | PANTHER rs3750920 (TOLLIP) Interaction* (n = 159**) | | | |
|---|---|---|---|---|
| | PAN (n = 39) | | NAC/Placebo (n = 120) | |
| | Minor Allele Present | Minor Allele Absent | Minor Allele Present | Minor Allele Absent |
| HR | 3.43 | 6.31 | 1.17 | 1 (Ref) |
| P-value | 0.001 | <0.001 | 0.7 | — |
| 95% CI | 1.62-7.27 | 2.43-16.3 | 0.73-1.87 | — |

*Based on multivariate Cox model adjusting for GAP score at the time of enrollment
**159/165 patients had genotype information for this SNP Conclusions: IPF-associated SNPs appear to be overrepresented in patients who participated in PANTHER compared to GWAS and SNP imbalance was detected between treatment arms. No SNP was found to be an independent predictor of composite endpoint risk, but the minor allele of rs3750920 (TOLLIP) appears to modify endpoint risk associated with PAN therapy. These findings underscore the need to delineate genetic factors contributing to death and disease progression. Accounting for these variables in future clinical trials may safeguard against unmeasured bias.

The foregoing description is considered as illustrative only of the principles of the invention. Further, since numerous modifications and changes will readily occur to those skilled in the art, it is not desired to limit the invention to the exact construction and process as described above. Accordingly, all suitable modifications and equivalents may be resorted to falling within the scope of the invention as defined by the claims that follow. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

REFERENCES

The following references, to the extent that they provide exemplary procedural or other details supplementary to those set forth herein, are specifically incorporated herein by reference.

1. Noth et al. *The Lancet.* 2013; 1(4):309-317.
2. Fingerlin et al. *Nat Genet.* 2013; 45(6):613-620.
3. Peljto et al. *JAMA: The Journal of the American Medical Association.* 2013; 309(21):2232-2239.
4. Zhang et al. *The Journal of Biological Chemistry.* 2002; 277(9):7059-7065.
5. Pruitt et al. *Nucleic Acids Research.* 2014; 42 (Database issue):D756-763.
6. Roy et al. *Nature.* 2014; 505(7483):412-416.
7. Shah et al. *J Immunol.* 2012; 189(4):1737-1746.
8. Saito et al. *Cell and Tissue Research.* 2005; 321(1):75-88.
9. Janardhan et al. *Histology and Histopathology.* 2006; 21(7):687-696.
10. Tang et al. *Journal of Clinical Microbiology.* 2003; 41(6):2633-2640.
11. Han et al. *Respiratory Medicine.* 2014; 2(7):548-556.
12. Hubbard et al. *Lancet.* 1996; 347(8997):284-289.
13. Molyneaux et al. *American Journal of Respiratory and Critical Care Medicine.* 2014; 190(8):906-913.
14. Asehnoune et al. *J Immunol.* 2004; 172(4):2522-2529.
15. De Flora et al. *The European Respiratory Journal.* 1997; 10(7):1535-1541.
16. Martinez et al. *N Engl J Med.* 2014; 370(22):2093-2101.
17. Raghu et al. *N Engl J Med.* 2012; 366(21):1968-1977.
18. King et al. *Lancet.* 2009; 374(9685):222-228.
19. Seibold et al. *N Engl J Med.* 2011; 364(16):1503-1512.
20. Raghu et al. *American Journal of Respiratory and Critical Care Medicine.* 2011; 183(6):788-824.
21. Johnson et al. *Bioinformatics.* 2008; 24(24):2938-2939.
22. Abecasis et al. *Nature.* 2012; 491(7422):56-65.
23. Raghu et al. *American Journal of Respiratory and Critical Care Medicine.* 2012; 185(10):1044-1048.
24. Perez-Giraldo et al. *The Journal of Antimicrobial Chemotherapy.* 1997; 39(5):643-646.
25. Oddera et al. *The Journal of Laboratory and Clinical Medicine.* 1994; 124(2):293-301.
26. Zhang et al. *The New England Journal of Medicine.* 2011; 364(16):1576-1577.

The invention claimed is:

1. A method for treating idiopathic pulmonary fibrosis (IPF) in a patient with N-acetylcysteine (NAC) comprising administering NAC to a patient after a sample from the patient has been genotyped and determined to be homozygous or heterozygous for a thymine at the single nucleotide polymorphism rs3750920.

2. A method for treating idiopathic pulmonary fibrosis (IPF) in a patient with a combination therapy comprising prednisone, azathioprine, and N-acetylcysteine (PAN) comprising administering PAN to a patient after a biological sample from the patient has been genotyped and determined to be homozygous or heterozygous for thymine at the single nucleotide polymorphism rs3750920.

3. The method of claim 2, wherein the nucleotide position corresponding to rs3750920 in the nucleotide coding sequence of TOLLIP has been sequenced.

4. The method of claim 2, wherein the patient was receiving one or more of N-acetylcysteine (NAC) or PAN therapy prior to genotyping.

5. The method of claim 3, wherein sequencing comprises amplifying a nucleic acid sequence complementary or identical to a region of the TOLLIP coding sequence comprising the nucleotide corresponding to rs3750920.

6. The method of claim 5, wherein amplifying comprises using polymerase chain reaction (PCR).

7. The method of claim 2, wherein the biological sample is a blood sample, a fecal sample, or a mouth swab.

8. The method of claim 2, wherein the biological sample comprises genomic DNA.

9. The method of claim 1, wherein the nucleotide position corresponding to rs3750920 in the nucleotide coding sequence of TOLLIP has been sequenced.

10. The method of claim 1, wherein the patient was receiving one or more of N-acetylcysteine (NAC) or PAN therapy prior to genotyping.

11. The method of claim 9, wherein sequencing comprises amplifying a nucleic acid sequence complementary or identical to a region of the TOLLIP coding sequence comprising the nucleotide corresponding to rs3750920.

12. The method of claim 11, wherein amplifying comprises using polymerase chain reaction (PCR).

13. The method of claim 1, wherein the sample is a blood sample, a fecal sample, or a mouth swab.

14. The method of claim 1, wherein the sample comprises genomic DNA.

* * * * *

SEQUENCE LISTING

<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
tttctctcat tgcctttga at                                     22

<210> SEQ ID NO 2
<211> LENGTH: 18
<212> TYPE: DNA
<213> ORGANISM: Artificial Sequence
<220> FEATURE:
<223> OTHER INFORMATION: Synthetic Primer

<400> SEQUENCE: 2
tctaacactg tcccttga                                         18

<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

<400> SEQUENCE: 3
atatacgatc gtgaagcc                                         18

<210> SEQ ID NO 4
<211> LENGTH: 17
<212> TYPE: DNA
<213> ORGANISM: Artificial Sequence
<220> FEATURE:
<223> OTHER INFORMATION: Synthetic Primer

<400> SEQUENCE: 4
ttcagcctca gtttacc                                          17

<210> SEQ ID NO 5
<211> LENGTH: 15
<212> TYPE: DNA
<213> ORGANISM: Artificial Sequence
<220> FEATURE:
<223> OTHER INFORMATION: Synthetic Primer

<400> SEQUENCE: 5
tccaccctgg aacag                                            15

<210> SEQ ID NO 6
<211> LENGTH: 16
<212> TYPE: DNA
<213> ORGANISM: Artificial Sequence
<220> FEATURE:
<223> OTHER INFORMATION: Synthetic Primer

<400> SEQUENCE: 6
gagacaccag aaggga                                           16

<210> SEQ ID NO 7
<211> LENGTH: 18
<212> TYPE: DNA
<213> ORGANISM: Artificial Sequence

```
<220> FEATURE:
<223> OTHER INFORMATION: Synthetic Primer

<400> SEQUENCE: 7
caaaagccag tcaagcag                                                 18

<210> SEQ ID NO 8
<211> LENGTH: 15
<212> TYPE: DNA
<213> ORGANISM: Artificial Sequence
<220> FEATURE:
<223> OTHER INFORMATION: Synthetic Primer

<400> SEQUENCE: 8
gtgagccctg ctgtt                                                    15

<210> SEQ ID NO 9
<211> LENGTH: 15
<212> TYPE: DNA
<213> ORGANISM: Artificial Sequence
<220> FEATURE:
<223> OTHER INFORMATION: Synthetic Primer

<400> SEQUENCE: 9
atgacggttg tcggc                                                    15

<210> SEQ ID NO 10
<211> LENGTH: 16
<212> TYPE: DNA
<213> ORGANISM: Artificial Sequence
<220> FEATURE:
<223> OTHER INFORMATION: Synthetic Primer

<400> SEQUENCE: 10
cccctttgtc tccact                                                   16

<210> SEQ ID NO 11
<211> LENGTH: 24
<212> TYPE: DNA
<213> ORGANISM: Artificial Sequence
<220> FEATURE:
<223> OTHER INFORMATION: Synthetic Primer

<400> SEQUENCE: 11
gttgttttat ctcaagtaca taca                                          24

<210> SEQ ID NO 12
<211> LENGTH: 15
<212> TYPE: DNA
<213> ORGANISM: Artificial Sequence
<220> FEATURE:
<223> OTHER INFORMATION: Synthetic Primer

<400> SEQUENCE: 12
acaggcccct ggtta                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic Primer

<400> SEQUENCE: 13
gtgttggtgc aggtg                                                    15
```

```
<210> SEQ ID NO 14
<211> LENGTH: 15
<212> TYPE: DNA
<213> ORGANISM: Artificial Sequence
<220> FEATURE:
<223> OTHER INFORMATION: Synthetic Primer

<400> SEQUENCE: 14
tggagtcgct ctggt                                                     15

<210> SEQ ID NO 15
<211> LENGTH: 17
<212> TYPE: DNA
<213> ORGANISM: Artificial Sequence
<220> FEATURE:
<223> OTHER INFORMATION: Synthetic Primer

<400> SEQUENCE: 15
tgacaccaaa caagtgg                                                   17

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
gagaaacaca gaaggaaatc                                                20

<210> SEQ ID NO 17
<211> LENGTH: 16
<212> TYPE: DNA
<213> ORGANISM: Artificial Sequence
<220> FEATURE:
<223> OTHER INFORMATION: Synthetic Primer

<400> SEQUENCE: 17
gagatccaga gaggga                                                    16

<210> SEQ ID NO 18
<211> LENGTH: 15
<212> TYPE: DNA
<213> ORGANISM: Artificial Sequence
<220> FEATURE:
<223> OTHER INFORMATION: Synthetic Primer

<400> SEQUENCE: 18
tatgggctca gtgcc                                                     15

<210> SEQ ID NO 19
<211> LENGTH: 15
<212> TYPE: DNA
<213> ORGANISM: Artificial Sequence
<220> FEATURE:
<223> OTHER INFORMATION: Synthetic Primer

<400> SEQUENCE: 19
tctgggcagt gggtt                                                     15

<210> SEQ ID NO 20
<211> LENGTH: 15
<212> TYPE: DNA
<213> ORGANISM: Artificial Sequence
<220> FEATURE:
<223> OTHER INFORMATION: Synthetic Primer
```

```
<400> SEQUENCE: 20
tggccagaat gaggg                                                    15
```